(12) United States Patent
Miyawaki et al.

(10) Patent No.: US 7,547,528 B2
(45) Date of Patent: Jun. 16, 2009

(54) FLUORESCENT PROTEIN AND CHROMOPROTEIN

(75) Inventors: Atsushi Miyawaki, Saitama (JP); Ryoko Ando, Saitama (JP); Satoshi Karasawa, Tokyo (JP); Hideaki Mizuno, Saitama (JP)

(73) Assignees: Riken, Saitama (JP); Medical & Biological Laboratories Co., Ltd., Aichi (JP)

( * ) Notice: Subject to any disclaimer, the term of this patent is extended or adjusted under 35 U.S.C. 154(b) by 0 days.

(21) Appl. No.: 12/016,903

(22) Filed: Jan. 18, 2008

(65) Prior Publication Data

US 2008/0227097 A1 Sep. 18, 2008

Related U.S. Application Data

(62) Division of application No. 10/525,365, filed as application No. PCT/JP03/10628 on Aug. 22, 2003, now Pat. No. 7,345,157.

(30) Foreign Application Priority Data

| Aug. 23, 2002 | (JP) | 2002-243337 |
| Aug. 23, 2002 | (JP) | 2002-243338 |
| Sep. 20, 2002 | (JP) | 2002-274266 |
| Sep. 26, 2002 | (JP) | 2002-280118 |

(51) Int. Cl.
*C12P 21/06* (2006.01)
*C12N 15/00* (2006.01)
*C12N 9/20* (2006.01)
*C07K 1/00* (2006.01)

(52) U.S. Cl. ............... 435/69.1; 536/23.1; 435/252.3; 435/320.1; 530/350

(58) Field of Classification Search ............... 536/23.1; 435/69.1, 252.3, 320.1
See application file for complete search history.

(56) References Cited

U.S. PATENT DOCUMENTS 6,933,375 B2 8/2005 Falkowski et al.
7,226,993 B2 6/2007 Miyawaki et al.
7,247,449 B2 7/2007 Miyawaki et al.
7,345,157 B2 3/2008 Miyawaki et al.
2006/0154296 A1 7/2006 Miyawaki et al.
2006/0240472 A1 10/2006 Miyawaki et al.
2007/0031912 A1 2/2007 Miyawaki et al.
2007/0072259 A1 3/2007 Miyawaki et al.
2007/0292909 A1 12/2007 Miyawaki et al.

FOREIGN PATENT DOCUMENTS

| WO | 00/34319 | 6/2000 |
| WO | 00/34526 | 6/2000 |
| WO | 01/27150 | 4/2001 |
| WO | 03/033693 | 4/2003 |
| WO | 03/054191 | 7/2003 |
| WO | 2004/111235 | 12/2004 |
| WO | 2004/111236 | 12/2004 |
| WO | 2005/054464 | 6/2005 |

OTHER PUBLICATIONS

Gurskaya et al. "GFP-like chromoproteins as a source of far-red fluorescent proteins" *FEBS Letters* 507(1):16-20 (2001).
Tsien, R.Y. "The Green Fluorescent Protein" *Ann. Rev. Biochem.* 67:509-544 (1998).
Wiedenmann et al. "Cracks in the β-can: Fluorescent proteins from *Anemonia sulcata* (Anthozoa, Actinaria)" *Proc. Natl. Acad. Sci. USA* 97(26):14091-14096 (2000).
Yanushevich et al. "A strategy for the generation of non-aggregating mutants of *Anthozoa* fluorescent proteins" *FEBS Letters* 511(1-3):11-14 (2002).
Ando et al. "An optical marker based on the UV-induced green-to-red photoconversion of a fluorescent protein" *Proc. Natl. Acad. Sci. USA* 99(20):12651-56 (2002).
U.S. Appl. No. 10/561,041 (Miyawaki et al.), the National Stage Entry of PCT/JP04/08786, filed Jun. 16, 2004 and entitled "Fluorescent Protein and Pigment Protein."

*Primary Examiner*—Maryam Monshipouri
(74) *Attorney, Agent, or Firm*—Greenblum & Bernstein, P.L.C.

(57) ABSTRACT

It is an object of the present invention to provide a novel chromoprotein and a novel fluorescent protein. The present invention provides chromoproteins derived from *Anthopleura inornata*, which have certain property, and fluorescent proteins from *Trachyphyllia geoffroyi* and *Scolymia vitiensis*, which have certain fluorescent property.

9 Claims, 16 Drawing Sheets

UV irradiation time (minute)
0  20  40  60  80  100  120  140

FLUORESCENT PROTEIN AND CHROMOPROTEIN

CROSS-REFERENCE TO RELATED APPLICATIONS

This application is a Divisional of application Ser. No. 10/525,365 filed Oct. 12, 2005 now U.S. Pat. No. 7,345,157, which is a National Stage of International Application No. PCT/JP2003/010628, filed Aug. 22, 2003.

This Application also claims priority of Japanese Application Nos. 2002-243337, filed Aug. 23, 2002, and 2002-243338, filed Aug. 23, 2002, and 2002-274266, filed Sep. 20, 2002, and 2002-280118, filed Sep. 26, 2002.

The entire disclosures of each of the above-cited applications, including application Ser. No. 10/525,365 and International Application No. PCT/JP2003/010628, are considered as being part of this application, and the entire disclosures of each of these applications are expressly incorporated by reference herein in their entireties.

TECHNICAL FIELD

The present invention relates to a novel chromoprotein. More specifically, the present invention relates to a novel chromoprotein derived from *Anthopleura inornata*, and the use thereof. The present invention relates to a novel fluorescent protein. More specifically, the present invention relates to a novel fluorescent protein derived from *Trachyphyllia geoffroyi* and *Scolymia vitiensis* and the use thereof.

BACKGROUND ART

Green fluorescent protein (GFP) derived from *Aequorea victoria*, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among *Aequorea*-derived GFP mutants, YFP exhibits the fluorescence with the longest wavelength. The values ε and Φ of the majority of YEPs are 60,000 to 100,000 $M^{-1}$ $cm^{-1}$ and 0.6 to 0.8, respectively (Tsien, R. Y. (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

In addition, cyan fluorescent protein (CFP) is another example of the GFP mutant. Of this type of protein, ECFP (enhanced cyan fluorescent protein) has been known. Moreover, red fluorescent protein (RFP) has been isolated from sea anemone (*Discoma* sp.). Of this type of protein, DasRed has been known. Thus, 4 types of fluorescent proteins, that are, green fluorescent protein, yellow fluorescent protein, cyan fluorescent protein, and red fluorescent protein, have successively been developed. The range of the spectrum has significantly been expanded.

A chromoprotein is a protein regarding which the quantum yield of the conventional fluorescent protein is reduced to close to zero. Since such a chromoprotein is capable of introducing into cells molecules that convert light energy into another type of energy, it can be applied to various purposes. However, there have been only a few reports regarding the absorption wavelength properties of such a chromoprotein.

DISCLOSURE OF THE INVENTION

It is an object of the present invention to provide a novel chromoprotein derived from *Anthopleura inornata*, which absorbs a light having a specific wavelength. It is another object of the present invention to provide a fluorescent protein having a novel primary structure, which is derived from Cnidaria, and particularly from *Trachyphyllia geoffroyi* and *Scolymia vitiensis* belonging to Scleractinia.

The present inventors have conducted intensive studies directed towards achieving the aforementioned object. They have designed suitable primers based on information regarding the amino acid sequences of known fluorescent proteins. Using these primers, they have succeeded in the amplification and cloning of genes encoding novel chromoproteins from the cDNA library of *Anthopleura inornata* exhibiting a green color. The present inventors have further analyzed the light-absorbing properties and pH sensitivity of the obtained chromoprotein derived from *Anthopleura inornata*.

Further, the present inventors have performed expression cloning by using cDNA library derived from *Trachyphyllia geoffroyi* and *Scolymia vitiensis*, and have succeeded in cloning genes encoding novel fluorescent proteins. The present inventors have examined the fluorescent properties of the obtained fluorescent proteins, and as a result, they have found that these fluorescent proteins have particular fluorescent properties.

The present invention has been completed based on these findings.

Thus, the present invention provides a chromoprotein derived from *Anthopleura inornata* having the following properties:
(1) the absorption maximum wavelength is 605 nm;
(2) the molar absorption coefficient is 47,550 at 605 nm; and
(3) the pH sensitivity of light-absorbing property is stable at between pH 5 and pH 10.

In another aspect of the present invention, there is provided a chromoprotein having either one of the following amino acid sequences:
(a) the amino acid sequence shown in SEQ ID NO: 1; and
(b) an amino acid sequence comprising a deletion, substitution and/or addition of one or several amino acids with respect to the amino acid sequence shown in SEQ ID NO: 1, and having light-absorbing properties.

In another aspect of the present invention, there is provided a chromoprotein derived from *Anthopleura inornata* having the following properties:
(1) the absorption maximum wavelength is 553 nm;
(2) the molar absorption coefficient is 25,300 at 553 nm; and
(3) the pH sensitivity of light-absorbing property is stable at between pH 5 and pH 10.

In another aspect of the present invention, there is provided a chromoprotein having either one of the following amino acid sequences:
(a) the amino acid sequence shown in SEQ ID NO: 3; and
(b) an amino acid sequence comprising a deletion, substitution and/or addition of one or several amino acids with respect to the amino acid sequence shown in SEQ ID NO: 3, and having light-absorbing properties.

In further another aspect of the present invention, there is provided a DNA encoding the protein of the present invention.

In further another aspect of the present invention, there is provided a DNA of either one of followings:
(a) DNA encoding the amino acid sequence shown in SEQ ID NO: 1; and
(b) DNA encoding a protein which has an amino acid sequence comprising a deletion, substitution and/or addition of one or several amino acids with respect to the amino acid sequence shown in SEQ ID NO: 1, and has light-absorbing properties.

In further another aspect of the present invention, there is provided a DNA of either one of followings:
(a) DNA encoding the amino acid sequence shown in SEQ ID NO: 3; and
(b) DNA encoding a protein which has an amino acid sequence comprising a deletion, substitution and/or addition of one or several amino acids with respect to the amino acid sequence shown in SEQ ID NO: 3, and has light-absorbing properties.

In further another aspect of the present invention, there is provided a DNA having either one of the following nucleotide sequences:
(a) the nucleotide sequence shown in SEQ ID NO: 2; and
(b) a nucleotide sequence comprising a deletion, substitution and/or addition of one or several nucleotides with respect to the nucleotide sequence shown in SEQ ID NO: 2, and encoding a protein having light-absorbing properties.

In further another aspect of the present invention, there is provided a DNA having either one of the following nucleotide sequences:
(a) the nucleotide sequence shown in SEQ ID NO: 4; and
(b) a nucleotide sequence comprising a deletion, substitution and/or addition of one or several nucleotides with respect to the nucleotide sequence shown in SEQ ID NO: 4, and encoding a protein having light-absorbing properties.

In further another aspect, the present invention provides a recombinant vector having the DNA of the present invention.

In further another aspect, the present invention provides a transformant having the DNA or recombinant vector of the present invention.

In further another aspect, the present invention provides a fusion protein composed of the chromoprotein of the present invention and another protein.

In further another aspect, the present invention provides a method for analyzing a physiologically active substance, which is characterized in that the FRET (fluorescence resonance energy transfer) method is applied using the chromoprotein of the present invention as an acceptor protein.

In further another aspect, the present invention provides a light-absorbing reagent kit comprising the chromoprotein, DNA, recombinant vector, transformant, or fusion protein of the present invention.

Further, the present invention provides a fluorescent protein derived from *Trachyphyllia geoffroyi*, which has the following properties:
(1) the color is changed from green to red by irradiation of ultraviolet ray; the excitation maximum wavelength is 508 nm (green) and 572 nm (red); and the fluorescence maximum wavelength is 518 nm (green) and 581 nm (red);
(2) the molar absorption coefficient (green) at 508 nm is 98800 $M^{-1}$ $cm^{-1}$; and the molar absorption coefficient (red) at 572 nm is 60400 $M^{-1}$ $cm^{-1}$;
(3) the quantum yield is 0.80 (green) and 0.33 (red); and
(4) pKa regarding the pH sensitivity of the green and red are both 5.7.

In another aspect of the present invention, there is provided a fluorescent protein having either one of the following amino acid sequences:
(a) an amino acid sequence shown in SEQ ID NO: 5; or
(b) an amino acid sequence comprising a deletion, substitution and/or addition of one or several amino acids with respect to the amino acid sequence shown in SEQ ID NO: 5, and having fluorescent properties.

In another aspect of the present invention, there is provided a fluorescent protein having an amino acid sequence shown in SEQ ID NO: 7.

In further another aspect of the present invention, there is provided a fluorescent protein derived from *Scolymia vitiensis*, which has the following properties:
(1) the color is changed from green to red by irradiation of ultraviolet ray; the excitation maximum wavelength is 508 nm (green) and 578 nm (red); and the fluorescence maximum wavelength is 518 nm (green) and 588 nm (red);
(2) the molar absorption coefficient (green) at 508 nm is 102250 $M^{-1}$ $cm^{-1}$; and the molar absorption coefficient (red) at 578 nm is 76950 $M^{-1}$ $cm^{-1}$;
(3) the quantum yield (fluorescence) is 0.43 (green) and 0.51 (red); and
(4) pKa regarding the pH sensitivity of the green (508 nm) is 5.8; and pKa regarding the pH sensitivity of the red (578 nm) is 6.5.

In another aspect of the present invention, there is provided a fluorescent protein having either one of the following amino acid sequences:
(a) an amino acid sequence shown in SEQ ID NO: 9; or
(b) an amino acid sequence comprising a deletion, substitution and/or addition of one or several amino acids with respect to the amino acid sequence shown in SEQ ID NO: 9, and having fluorescent properties.

In another aspect of the present invention, there is provided a fluorescent protein having an amino acid sequence shown in any of SEQ ID NO: 11, 13, 15 or 17.

In further another aspect of the present invention, there is provided a DNA of either one of the following:
(a) DNA which encodes the amino acid sequence shown in SEQ ID NO: 5; or
(b) DNA which encodes an amino acid sequence comprising a deletion, substitution and/or addition of one or several amino acids with respect to the amino acid sequence shown in SEQ ID NO: 5, and encodes a fluorescent protein:
(c) DNA having a nucleotide sequence shown in SEQ ID NO: 6; or
(d) DNA having a nucleotide sequence comprising a deletion, substitution and/or addition of one or several nucleotides with respect of the nucleotide sequence shown in SEQ ID NO: 6, and encoding a fluorescent protein.

In further another aspect of the present invention, there is provided a DNA of either one of the following:
(a) DNA which encodes the amino acid sequence shown in SEQ ID NO: 7; or
(b) DNA having a nucleotide sequence shown in SEQ ID NO: 8.

In further another aspect of the present invention, there is provided a DNA of either one of the following:
(a) DNA which encodes the amino acid sequence shown in SEQ ID NO: 9; or
(b) DNA which encodes an amino acid sequence comprising a deletion, substitution and/or addition of one or several amino acids with respect to the amino acid sequence shown in SEQ ID NO: 9, and encodes a fluorescent protein:
(c) DNA having a nucleotide sequence shown in SEQ ID NO: 10; or (d) DNA having a nucleotide sequence comprising a deletion, substitution and/or addition of one or several nucleotides with respect to the nucleotide sequence shown in SEQ ID NO: 10, and encoding a fluorescent protein.

In further another aspect of the present invention, there is provided a DNA of either one of the following:
(a) DNA which encodes the amino acid sequence shown in SEQ ID NO: 11, 13, 15 or 17; or
(b) DNA having a nucleotide sequence shown in SEQ ID NO: 12, 14, 16 or 18.

In further another aspect of the present invention, there is provided a recombinant vector having any of the DNA of the present invention.

In further another aspect of the present invention, there is provided a transformant having the DNA or recombinant vector of the present invention.

In further another aspect of the present invention, there is provided a fusion fluorescent protein consisting of the fluorescent protein of the present invention and another protein. Preferably, said another protein is one that localizes in the cell, and more preferably one specific to an intracellular organella.

In further another aspect of the present invention, there is provided a method for analyzing the localization or dynamics of a protein in cells, characterized in that the fusion protein of the present invention is allowed to be expressed in cells.

In further another aspect of the present invention, there is provided a fluorescent reagent kit which comprises the fluorescent proteins, DNAs, recombinant vector, transformant or fusion protein of the present invention.

Irradiation at 410 nm, measurement of the green fluorescence, and measurement of the red fluorescence were carried out at intervals of 3 seconds.

Measurement was carried out under the aforementioned conditions, and the fluorescence values of the red fluorescence and the green fluorescence were expressed in a graph.

Figure 24:
Figure 25:
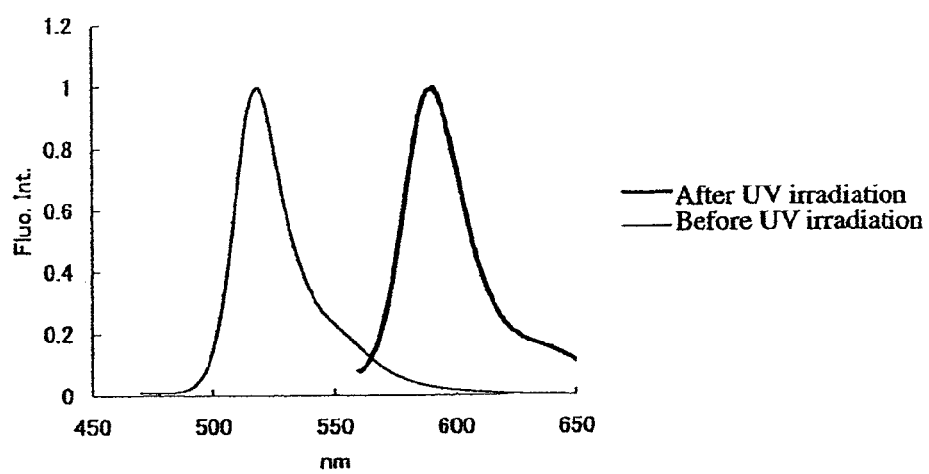
Figure 26:
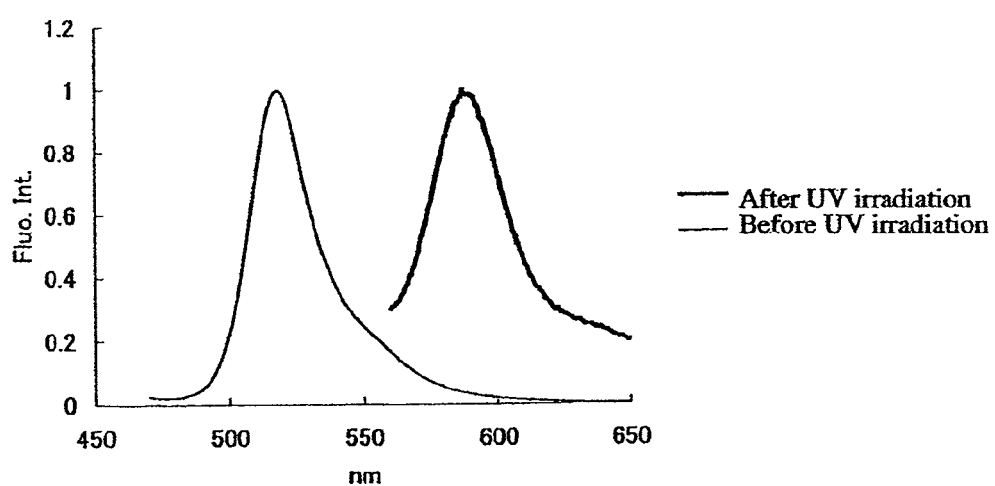

FIG. 24 shows the results obtained by exciting with a blue light the electrophoretic pattern on 12.5% acrylamide gel (Pseudo-native SDS/PAGE) and then photographing the resultant with a digital camera.
WT (Momiji): tetramer
d16: dimer
m16: monomer FIG. 25 shows the fluorescence spectrum (d16) before and after irradiation with light at 365 nm.
Green fluorescence peak: 518 nm
Red fluorescence peak: 591 nm FIG. 26 shows the fluorescence spectrum (m16) before and after irradiation with light at 365 nm.
Green fluorescence peak: 518 nm
Red fluorescence peak: 587 nm

BEST MODE FOR CARRYING OUT THE INVENTION

The embodiments of the present invention will be described in detail below.

(1) Chromoprotein of the Present Invention

The first chromoprotein of the present invention is characterized in that it is derived from *Anthopleura inornata*, and has the following properties:
(1) the absorption maximum wavelength is 605 nm;
(2) the molar absorption coefficient is 47,550 at 605 nm; and
(3) the pH sensitivity of light-absorbing property is stable at between pH 5 and pH 10.

The second chromoprotein of the present invention is characterized in that it is derived from *Anthopleura inornata*, and has the following properties:
(1) the absorption maximum wavelength is 553 nm;
(2) the molar absorption coefficient is 25,300 at 553 nm; and
(3) the pH sensitivity of light-absorbing property is stable at between pH 5 and pH 10.

*Anthopleura inornata* has 96 tentacles, which are regularly aligned. In addition, this species is characterized in that it has an oral disc having the same color as that of the tentacles and that the surrounding portion of the mouth has a reddish brown color. 98 lines of adhesive warts are found on the body wall, and such warts are distributed up to the lower end of the body wall. The color of the body wall is largely varied, and brown, blue, and pink body colors have been known. Such *Anthopleura inornata* ranges from the southern part of Hokkaido to Kyushu, and many of them live in the intertidal zone.

In the examples described later in the present specification, a chromoprotein having the aforementioned properties was isolated from *Anthopleura inornata* that was used as a starting material. However, there may also be cases where the chromoprotein of the present invention can be obtained from a sea anemone other than *Anthopleura inornata*. The thus obtained chromoprotein is also included in the scope of the present invention.

As described in the examples below, the first chromoprotein (Be-G) of the present invention has an absorption maximum wavelength of 605 nm, and the molar absorption coefficient is 47,550 at 605 nm.

As described in the examples below, the second chromoprotein (Be-R) of the present invention has an absorption maximum wavelength of 553 nm, and the molar absorption coefficient is 25,300 at 553 nm.

The molar absorption coefficient represents the amount of absorbed photons per mole of molecule, and the quantum yield represents a numerical value showing the amount of the absorbed photons that can be emitted as fluorescence. Since the chromoproteins of the present invention have an extremely low quantum yield, they hardly emit fluorescence at all. Due to this property, the chromoproteins of the present invention can be used: (1) as an acceptor molecule (energy receptor) in FRET; (2) in development of a system for converting the energy of applied light into energy other than the light; and (3) in introduction of a mutation into the amino acid sequence of the protein to modify it so that it emits fluorescence.

In addition, the chromoproteins of the present invention are characterized in that the pH sensitivity of light-absorbing properties is stable at between pH 5 and pH 10. That is to say, in the case of the chromoproteins of the present invention, the peak value of the absorption spectrum does not significantly fluctuate in the range between pH 5 and pH 10. Accordingly, even under the same conditions, the chromoproteins of the present invention can be used in a broad range of pH environments, and thus, the use of the chromoproteins in vivo have few restrictions.

The examples of the chromoprotein of the present invention include a chromoprotein having either one of the following amino acid sequences:
(a) the amino acid sequence shown in SEQ ID NO: 1 or 3; and
(b) an amino acid sequence comprising a deletion, substitution and/or addition of one or several amino acids with respect to the amino acid sequence shown in SEQ ID NO: 1 or 3, and having light-absorbing properties.

The scope of "one or several" in the phrase "an amino acid sequence comprising a deletion, substitution and/or addition of one or several amino acids" is not particularly limited in the present specification. For example, it means 1 to 20, preferably 1 to 10, more preferably 1 to 7, further preferably 1 to 5, and particularly preferably 1 to 3.

The term "light-absorbing properties" is used in the present specification to mean properties capable of absorbing light having a certain wavelength. For example, an absorption maximum wavelength may be 605 nm or 553 nm as in the case of the chromoproteins described in the present specification, or the value of the absorption maximum wavelength may also be shifted. It is preferable that the pH sensitivity of light-absorbing properties is stable at between pH 5 and pH 10.

The chromoproteins of the present invention having the amino acid sequence shown in SEQ ID NO: 1 or 3 in the sequence listing hardly emit fluorescence at all. In the present invention, one or several amino acids are deleted, substituted, and/or added with respect to the amino acid sequence shown in SEQ ID NO: 1 or 3, so as to produce a protein having stronger fluorescence. The thus produced proteins are also included in the scope of the present invention.

The method of obtaining the chromoproteins of the present invention is not particularly limited. The proteins may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence shown in SEQ ID NO: 1 or 3 of the sequence listing of the present specification and the nucleotide sequence shown in SEQ ID NO: 2 or 4 thereof. Using these primers, PCR is carried out by using cDNA library derived from *Anthopleura inornata* as a template, so that DNA encoding the chromoprotein of the present invention can be obtained. The chromoprotein of the present invention can be produced by introducing this DNA into an appropriate expression system. Expression in an expression system will be described later in the present specification.

(2) Fluorescent Protein of the Present Invention

The first fluorescent protein of the present invention is characterized in that it is derived from *Trachyphyllia geoffroyi* and has the following properties:
(1) the color is changed from green to red by irradiation of ultraviolet ray; the excitation maximum wavelength is 508 nm (green) and 572 nm (red); and the fluorescence maximum wavelength is 518 nm (green) and 581 nm (red);
(2) the molar absorption coefficient (green) at 508 nm is 98800 $M^{-1}$ $cm^{-1}$; and the molar absorption coefficient (red) at 572 nm is 60400 $M^{-1}$ $cm^{-1}$;
(3) the quantum yield is 0.80 (green) and 0.33 (red); and
(4) pKa regarding the pH sensitivity of the green and red are both 5.7.

*Trachyphyllia geoffroyi* is one type of cnidarian sea anemone, and it is characterized in that it emits extremely colorful fluorescence. *Trachyphyllia geoffroyi* mainly ranges over the area below the midland of Honshu Island, Japan. This sea anemone lives in the sludge in the gulf. At night, it extends its tentacles to capture plankton and the like. In terms of a color variation, green, brown, and red examples are found.

As shown in the examples later, the color of the first fluorescent protein of the present invention is changed from green to red by irradiation of ultraviolet ray; the excitation maximum wavelength is 508 nm (green) and 572 nm (red); and the fluorescence maximum wavelength is 518 nm (green) and 581 nm (red). The molar absorption coefficient (green) at 508 nm is 98800 $M^{-1}$ $cm^{-1}$; and the molar absorption coefficient (red) at 572 nm is 60400 $M^{-1}$ $cm^{-1}$;

The first fluorescent protein of the present invention is characterized in that its color changes due to ultraviolet rays. Thus, optical marking can be carried out on specific cells or organs thereof.

The examples of the first fluorescent protein of the present invention include a fluorescent protein having either one of the following amino acid sequences:
(a) an amino acid sequence shown in SEQ ID NO: 5; or
(b) an amino acid sequence comprising a deletion, substitution and/or addition of one or several amino acids with respect to the amino acid sequence shown in SEQ ID NO: 5, and having fluorescent properties.

Other examples of the first fluorescent protein of the present invention include a fluorescent protein having an amino acid sequence shown in SEQ ID NO: 7.

The second fluorescent protein of the present invention is characterized in that it is derived from *Scolymia vitiensis* and has the following properties:
(1) the color is changed from green to red by irradiation of ultraviolet ray; the excitation maximum wavelength is 508 nm (green) and 578 nm (red); and the fluorescence maximum wavelength is 518 nm (green) and 588 nm (red);
(2) the molar absorption coefficient (green) at 508 nm is 102250 $M^{-1}$ $cm^{-1}$; and the molar absorption coefficient (red) at 578 nm is 76950 $M^{-1}$ $cm^{-1}$;
(3) the quantum yield (fluorescence) is 0.43 (green) and 0.51 (red); and
(4) pKa regarding the pH sensitivity of the green (508 nm) is 5.8; and pKa regarding the pH sensitivity of the red (578 nm) is 6.5.

*Scolymia vitiensis* is a sessile single coral. A small individual has a pot-like round shape. However, after it has matured, it has an oval shape. A large spongy columella is found in the center of a coral individual, and a long barrier extends at an almost constant slope from the theca towards the center. A large serration is located on the barrier, and such serration can be seen from the outside. This coral does not open its polyp during the day. It generally has a dark green color, but it also has a red color in rare cases. Approximately 4 types of *Scolymia vitiensis* have been known. Among them, only one type ranges in the ocean areas surrounding Japan.

As shown in the examples later, the color of the second fluorescent protein of the present invention is changed from green to red by irradiation of ultraviolet ray; the excitation maximum wavelength is 508 nm (green) and 578 nm (red); and the fluorescence maximum wavelength is 518 nm (green) and 588 nm (red). The molar absorption coefficient (green) at 508 nm is 102250 $M^{-1}$ $cm^{-1}$; and the molar absorption coefficient (red) at 578 nm is 76950 $M^{-1}$ $cm^{-1}$.

The first fluorescent protein of the present invention is characterized in that its color changes due to ultraviolet rays. Thus, optical marking can be carried out on specific cells or organs thereof.

The examples of the second fluorescent protein of the present invention include a fluorescent protein having either one of the following amino acid sequences:
(a) an amino acid sequence shown in SEQ ID NO: 9; or
(b) an amino acid sequence comprising a deletion, substitution and/or addition of one or several amino acids with respect to the amino acid sequence shown in SEQ ID NO: 9, and having fluorescent properties.

Other examples of the first fluorescent protein of the present invention include a fluorescent protein having an amino acid sequence shown in any of SEQ ID NO: 11, 13, 15 or 17.

The scope of "one or several" in the phrase "an amino acid sequence comprising a deletion, substitution and/or addition of one or several amino acids" is not particularly limited in the present specification. For example, it means 1 to 20, preferably 1 to 10, more preferably 1 to 7, further preferably 1 to 5, and particularly preferably 1 to 3.

The term "having fluorescent properties" covers all of the cases where any fluorescence is given. Various properties such as fluorescence intensity, excitation wavelength, fluorescence wavelength or pH sensitivity, may be changed or may remain unchanged.

The method of obtaining the fluorescent protein of the present invention is not particularly limited. The protein may be either a protein synthesized by chemosynthesis, or recombinant protein produced by a gene recombination technique.

Where a recombinant protein is produced, it is necessary to obtain DNA encoding the protein. Appropriate primers are designed by using information regarding the amino acid sequence shown in SEQ ID NOS: 5, 7, 9, 11, 13, 15 or 17 of the sequence listing of the present specification and the nucleotide sequence shown in SEQ ID NOS: 6, 8, 10, 12, 14, 16 or 18 thereof. Using these primers, PCR is carried out by using cDNA clones of the above-described various types of known fluorescent proteins as a template, so that DNA encoding the fluorescent protein of the present invention can be obtained. Where a partial fragment of DNA encoding the fluorescent protein of the present invention are obtained by the above-described PCR, the produced DNA fragments are ligated to one another by a gene recombination technique, so that DNA encoding the desired fluorescent protein can be obtained. The fluorescent protein of the present invention can be produced by introducing this DNA into an appropriate expression system. Expression in an expression system will be described later in the present specification.

(3) DNA of the Present Invention

According to the present invention, genes encoding the chromoproteins and fluorescent proteins of the present invention are provided.

Specific examples of DNA encoding the first chromoprotein of the present invention may include either one of the following DNAs:
(a) DNA encoding the amino acid sequence shown in SEQ ID NO: 1; and
(b) DNA encoding a protein which has an amino acid sequence comprising a deletion, substitution and/or addition of one or several amino acids with respect to the amino acid sequence shown in SEQ ID NO: 1, and has light-absorbing properties.

Other examples of DNA encoding the first chromoprotein of the present invention may include either one of the following DNAs:
(a) the nucleotide sequence shown in SEQ ID NO: 2; and
(b) a nucleotide sequence comprising a deletion, substitution and/or addition of one or several nucleotides with respect to the nucleotide sequence shown in SEQ ID NO: 2, and encoding a protein having light-absorbing properties.

Specific examples of DNA encoding the second chromoprotein of the present invention may include either one of the following DNAs:
(a) DNA encoding the amino acid sequence shown in SEQ ID NO: 3; and
(b) DNA encoding a protein which has an amino acid sequence comprising a deletion, substitution and/or addition of one or several amino acids with respect to the amino acid sequence shown in SEQ ID NO: 3, and has light-absorbing properties.

Other examples of DNA encoding the second chromoprotein of the present invention may include either one of the following DNAs:
(a) the nucleotide sequence shown in SEQ ID NO: 4; and
(b) a nucleotide sequence comprising a deletion, substitution and/or addition of one or several nucleotides with respect to the nucleotide sequence shown in SEQ ID NO: 4, and encoding a protein having light-absorbing properties.

Specific examples of DNA encoding the first fluorescent protein of the present invention may include either one of the following DNAs:
(a) DNA which encodes the amino acid sequence shown in SEQ ID NO: 5; or
(b) DNA which encodes an amino acid sequence comprising a deletion, substitution and/or addition of one or several amino acids with respect to the amino acid sequence shown in SEQ ID NO: 5, and encodes a fluorescent protein:

(c) DNA having a nucleotide sequence shown in SEQ ID NO: 6; or
(d) DNA having a nucleotide sequence comprising a deletion, substitution and/or addition of one or several nucleotides with respect of the nucleotide sequence shown in SEQ ID NO: 6, and encoding a fluorescent protein.

Other examples of DNA encoding the first fluorescent protein of the present invention may include either one of the following DNAs:
(a) DNA which encodes the amino acid sequence shown in SEQ ID NO: 7; or
(b) DNA having a nucleotide sequence shown in SEQ ID NO: 8.

Specific examples of DNA encoding the second fluorescent protein of the present invention may include either one of the following DNAs:
(a) DNA which encodes the amino acid sequence shown in SEQ ID NO: 9; or
(b) DNA which encodes an amino acid sequence comprising a deletion, substitution and/or addition of one or several amino acids with respect to the amino acid sequence shown in SEQ ID NO: 9, and encodes a fluorescent protein:
(c) DNA having a nucleotide sequence shown in SEQ ID NO: 10; or
(d) DNA having a nucleotide sequence comprising a deletion, substitution and/or addition of one or several nucleotides with respect of the nucleotide sequence shown in SEQ ID NO: 10, and encoding a fluorescent protein.

Other examples of DNA encoding the second fluorescent protein of the present invention may include either one of the following DNAs:
(a) DNA which encodes the amino acid sequence shown in SEQ ID NO: 11, 13, 15 or 17; or
(b) DNA having a nucleotide sequence shown in SEQ ID NO: 12, 14, 16 or 18.

The DNA of the present invention can be synthesized by, for example, the phosphoramidite method, or it can also be produced by polymerase chain reaction (PCR) using specific primers. The DNA of the present invention is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory Manual, $2^{nd}$ Ed., Cold Spring Harbor Laboratory, Cold Spring Harbor, N.Y., 1989; and Current Protocols in Molecular Biology, Supplements 1 to 38, John Wiley & Sons (1987-1997).

(4) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4-c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(5) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells.

A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Shizosaccharomyces*. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to *Filamentous fungi* such as *Aspergillus, Neurospora, Fusarium* or *Trichoderma*. Where *Filamentous fungi* are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(6) Use of the Chromoprotein of the Present Invention and a Fusion Protein Comprising the Same The chromoprotein of the present invention can be fused with another protein, so as to construct a fusion protein. The type of said another protein to be fused to the chromoprotein of the present invention is not particularly limited, and preferred examples may include a protein which interacts with another molecule. The examples may include a receptor protein or ligand thereof, antigen, antibody and the like.

A method of obtaining the fusion protein of the present invention is not particularly limited. It may be either a protein synthesized by chemosynthesis, or recombinant protein produced by a gene recombination technique.

Where a recombinant fusion protein is produced, it is necessary to obtain DNA encoding the protein. The DNA encoding the chromoprotein of the present invention and the DNA encoding the another protein to be fused to the chromoprotein, can be obtained by the method as mentioned above in this specification or by the method similar to it. Then, these DNA fragments are ligated to one another by a gene recombination technique, so that DNA encoding the desired fusion protein can be obtained. This DNA is then introduced into an appropriate expression system, so that the fusion protein of the present invention can be produced.

FRET (fluorescence resonance energy transfer) has been known as a means for analyzing the interaction between molecules. In FRET, for example, a first molecule labeled with a cyan fluorescent protein (CFP) acting as a first fluorescent protein is allowed to coexist with a second molecule labeled with a yellow fluorescent protein (YFP) acting as a second fluorescent protein, so as to allow the yellow fluorescent protein (YFP) to act as an acceptor molecule and to allow the cyan fluorescent protein (CFP) to act as a donor molecule. Thus, FRET (fluorescence resonance energy transfer) is allowed to take place between both molecules, so as to visualize the interaction between the first and second molecules. Namely, in FRET, different dyes are introduced into two types of molecules. One dyes with a higher energy level (a donor molecule) is selectively excited, and the fluorescence of the dye is measured. Long-wavelength fluorescence from the other dye (an acceptor molecule) is also measured. The interaction between the molecules is visualized by using the difference between the amounts of both fluorescences. Only when both dyes are adjacent to each other due to the interaction of the two types of molecules, a decrease in the fluorescence of the donor molecule and an increase in the fluorescence of the acceptor molecule are observed by single wavelength excitation dual wavelength photometry. However, in a case where a chromoprotein is used as an acceptor molecule, a decrease in the fluorescence of the donor molecule occurs only when both dyes are adjacent to each other by the interaction of the two types of molecules. Such a decrease can be observed by single wavelength excitation single wavelength photometry. Thus, the use of the chromoprotein of the present invention enables facilitation of measurement apparatuses.

The chromoprotein of the present invention is particularly advantageous when it is used as an acceptor molecule in FRET (fluorescence resonance energy transfer). That is to say, a fused form (a first fused form) of the chromoprotein of the present invention and a test substance is first produced. Then, a fused form (a second fused form) of another test substance interacting with the above test substance and another fluorescent protein is produced. Thereafter, the first fused form is allowed to interact with the second fused form, and the generated fluorescence is analyzed, so that the interaction between the aforementioned two types of test substances can be analyzed. FRET (fluorescence resonance energy transfer) using the chromoprotein of the present invention may be carried out either in a test tube or in a cell.

(7) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or recombinant protein produced by a gene recombination technique.

Where a recombinant protein is produced, it is necessary to obtain DNA encoding the protein. Appropriate primers are designed using the information regarding the amino acid sequence shown in SEQ ID NO: 5, 7, 9, 11, 13, 15 or 17 of the sequence listing of the present specification and the nucleotide sequence shown in SEQ ID NO: 6, 8, 10, 12, 14, 16 or 18 thereof. Using these primers, PCR is carried out using a DNA fragment containing the gene of the fluorescent protein of the present invention as a template, so as to produce DNA fragments necessary for construction of the DNA encoding the fluorescent protein of the present invention. Moreover, DNA fragment encoding a protein to be fused is also obtained in the same above manner.

Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae, Escherichia coli* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

A filter set can be appropriately selected depending on the fluorescence wavelength of a fluorescent protein. In the case of the first fluorescent protein of the present invention, when the green having the excitation maximum wavelength of 508 nm and the fluorescence maximum wavelength of 518 nm is detected, a filter having an excitation light between approximately 490 and 510 nm and a fluorescence between approximately 510 and 530 nm can be preferably used. Also, when the red having the excitation maximum wavelength of 572 nm and the fluorescence maximum wavelength of 581 nm is detected, a filter having an excitation light between approximately 560 and 575 nm and a fluorescence between approximately 575 and 590 nm can be preferably used.

In the case of the second fluorescent protein of the present invention, when the green having the excitation maximum wavelength of 508 nm and the fluorescence maximum wavelength of 518 nm is detected, a filter having an excitation light between approximately 490 and 510 nm and a fluorescence between approximately 510 and 530 nm can be preferably used. Also, when the red having the excitation maximum wavelength of 578 nm and the fluorescence maximum wavelength of 588 nm is detected, a filter having an excitation light between approximately 570 and 580 nm and a fluorescence between approximately 580 and 595 nm can be preferably used.

When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

(8) Kit of the Present Invention

The present invention provides a light-absorbing reagent kit comprising at least one which is selected from the chromoprotein, fusion protein, DNA, recombinant vector or transformant, which are described in the present specification. Further, the present invention provides a kit for analyzing the localization of intracellular components and/or analyzing physiologically active substances, which is characterized in that it comprises at least one selected from the fluorescent protein, the fusion fluorescent protein, the DNA, the recombinant vector, or the transformant, which are described in the present specification. The kit of the present invention can be produced from commonly used materials that are known per se, by using common methods.

Reagents such as the chromoprotein, the fluorescent protein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example A-1

Isolation of Gene Encoding Novel Chromoprotein from Sea Anemone (1) Extraction of Total RNA A chromoprotein gene was isolated from sea anemone. One individual of *Anthopleura inornata* emitting a green color was used as a material. Frozen *Anthopleura inornata* was crushed in a mortar. 7.5 ml of "TRIzol" (GIBCO BRL) was added to 1 g (wet weight) of *Anthopleura inornata*, and the mixture was homogenized, followed by centrifugation at 1,500×g for 10 minutes. 1.5 ml of chloroform was added to the supernatant. The mixture was stirred for 15 seconds and then left at rest for 3 minutes. The resultant product was centrifuged at 7,500×g for 15 minutes. 3.75 ml of isopropanol was added to the supernatant. The mixture was stirred for 15 seconds and then left at rest for 10 minutes. The resultant product was centrifuged at 17,000×g for 10 minutes. The supernatant was discarded, and 6 ml of 70% ethanol was added thereto. The obtained mixture was centrifuged at 17,000×g for 10 minutes. The supernatant was discarded, and the precipitate was dissolved in 200 μl of DEPC water. Total RNA dissolved in the DEPC water was 100 times diluted, and the values of O.D.260 and O.D.280 were measured, so as to determine the concentration of RNA. 2.2 mg of the total RNA was obtained.

(2) Synthesis of First Stand cDNA cDNA (33 μl) was synthesized from 4 μg of the total RNA using a kit for synthesizing first strand cDNA, "Ready To Go" (Amersham Pharmacia).

(3) Degenerated PCR

Using 3 μl out of the synthesized first strand cDNA (33 μl) as a template, PCR was carried out. Primers were designed and produced by comparing the amino acid sequences of known fluorescent proteins, extracting similar portions, and converting them into nucleotide sequences. The sequences of the used primers are shown below:

```
                                            (SEQ ID NO: 19)
5'-GAAGGRTGYGTCAAYGGRCAY-3' (primer1)

(SEQ ID NO: 20)
5'-ACVGGDCCATYDGVAAGAAARTT-3' (primer2)
``` wherein R represents A or G, Y represents C or T, V represents A, C or G, and D represents A, G or T.

| Composition of PCR reaction solution | |
|---|---|
| Template (first strand cDNA) | 3 μl |
| ×10 taq buffer | 5 μl |
| 2.5 mM dNTPs | 4 μl |
| 100 uM primer 1 | 1 μl |
| 100 uM primer 2 | 1 μl |
| Milli Q | 35 μl |
| Taq polymerase (5 U/μl) | 1 μl |

| RCR reaction conditions | |
|---|---|
| 94° C., | 1 minute (PAD) |
| 94° C., | 30 seconds (denaturation) |
| 52° C., | 30 seconds (annealing of the primers to the template) |
| 72° C., | 1 minute (elongation of the primers) |

30 cycles consisting of the above 3 steps were carried out. The annealing temperature was decreased 0.3° C. per cycle. That is to say, the annealing temperature in the 30$^{th}$ cycle was 43° C.
72° C., 7 minutes (final elongation)
Retention at 4° C.

Using 1 μl of an amplified product obtained as a result of the first PCR reaction as a template, PCR was carried out once again under the same conditions. A 350-bp fragment was cut out by agarose gel electrophoresis and then purified.

(4) Subcloning and Sequencing

The purified DNA fragment was ligated to a pT7-blue vector (Novagen). *Escherichia coli* (TG1) was transformed with the vector, and the obtained transformants were subjected to blue white selection. Thereafter, plasmid DNA was purified from white colonies of *Escherichia coli*. The nucleotide sequence of the inserted DNA fragment was determined by a DNA sequencer. The obtained nucleotide sequence was compared with the nucleotide sequences of other fluorescent protein genes to confirm that the nucleotide sequence of the DNA was derived from a fluorescent protein. 5'-RACE and 3'-RACE methods were applied to a gene that had been confirmed to be a part of a fluorescent protein gene, so as to carry out the cloning of a full-length gene.

(5) 5'-RACE Method

In order to determine the nucleotide sequence of the 5'-terminal side of the DNA fragment obtained by degenerated PCR, the 5'-RACE method was applied using 5'-RACE System for Rapid Amplification of cDNA Ends, Version 2.0 (GIBCO BRL). 4 μg of the total RNA prepared in (1) above was used as a template.

For the first amplification of dC-tailed cDNA, the following primers were used:

```
                                            (SEQ ID NO: 21)
5'-ggccacgcgtcgactagtacgggnngggnngggnng-3'
(primer3)

(SEQ ID NO: 22)
5'-AAGAGACTCCTTGAAGTAATCGGGA-3' (primer4)
``` wherein n represents inosine.

For the second amplification, the following primers were used:

```
                                            (SEQ ID NO: 23)
5'-ggccacgcgtcgactagtac-3' (primer5)

(SEQ ID NO: 24)
5'-AAAATATCGTACGCAAAGGG-3' (primer6)
```

PCR reaction conditions and the like were determined in accordance with the protocols attached with the kit.

The 200-bp amplified band was cut out by agarose gel electrophoresis and then purified. The purified DNA fragment was ligated to a pT7-blue vector (Novagen). *Escherichia coli* (TG1) was transformed with the vector, and the obtained transformants were subjected to blue white selection. Thereafter, plasmid DNA was purified from white colonies of *Escherichia coli*. The nucleotide sequence of the inserted DNA fragment was determined by a DNA sequencer.

(6) 3'-RACE Method

The 3'-terminal portion of the DNA fragment obtained by degenerated PCR was obtained by PCR, using the primer produced based on the information obtained by sequencing of the nucleotide sequence in (4) above and an oligo dT primer. 3 μl of the first strand cDNA prepared in (2) above was used as a template. The produced primer is shown below:

```
                                            (SEQ ID NO: 25)
5'-AGGAGGTCCGCTACCCTTTG-3' (primer7)
```

| Composition of PCR reaction solution | |
|---|---|
| Template (first strand cDNA) | 3 μl |
| ×10 taq buffer | 5 μl |
| 2.5 mM dNTPs | 4 μl |
| 20 μM primer 7 | 1 μl |
| 10 μM oligo dT primer | 1 μl |
| Milli Q | 35 μl |
| Taq polymerase (5 U/μl) | 1 μl |

| RCR reaction conditions | |
|---|---|
| 94° C., | 1 minute (PAD) |
| 94° C., | 30 seconds (denaturation) |
| 52° C., | 30 seconds (annealing of the primers to the template) |
| 72° C., | 1 minute (elongation of the primers) |
| 30 cycles consisting of the above 3 steps were carried out. | |
| 72° C., | 7 minutes (final elongation) |
| Retention at 4° C. | |

An amplified band of approximately 1,000 bp was cut out by agarose gel electrophoresis and then purified. The purified DNA fragment was ligated to a pT7-blue vector (Novagen).

Escherichia coli (TG1) was transformed with the vector, and the obtained transformants were subjected to blue white selection. Thereafter, plasmid DNA was purified from white colonies of Escherichia coli. The nucleotide sequence of the inserted DNA fragment was determined by a DNA sequencer. The obtained full-length nucleotide sequence is shown in SEQ ID NO: 2, and the obtained full-length amino acid sequence is shown in SEQ ID NO: 1.

Example A-2

Expression of Protein in Escherichia coli

A primer corresponding to the N-terminal of the protein was produced from the obtained full-length nucleotide sequence, and an oligo dT primer was used for C-terminal. PCR was carried out using these primers and the first strand cDNA prepared in Example A-1 (2) as a template. The used primers are as follows:

```
                                              (SEQ ID NO: 26)
5'-CCCGGATCCGACCATGGCTACCTTGGTTAAAGA-3'  (primer8)
```

| Composition of PCR reaction solution | |
|---|---|
| Template (first strand cDNA) | 3 μl |
| x10 pyrobest buffer | 5 μl |
| 2.5 mM dNTPs | 4 μl |
| 100 μM primer 8 | 1 μl |
| 100 μM oligo dT primer | 1 μl |
| Milli Q | 35 μl |
| Pyrobest polymerase (5 U/μl) | 1 μl |

| RCR reaction conditions | |
|---|---|
| 94° C., | 1 minute (PAD) |
| 94° C., | 30 seconds (denaturation) |
| 52° C., | 30 seconds (annealing of the primers to the template) |
| 72° C., | 1 minute (elongation of the primers) |
| 30 cycles consisting of the above 3 steps were carried out. | |
| 72° C., | 7 minutes (final elongation) |
| Retention at 4° C. | |

An amplified band of approximately 1100 bp was cut out by agarose gel electrophoresis and then purified. The purified DNA fragment was subcloned into the BamHI-EcoRI site of a pRSET vector (Invitrogen), and it was then allowed to express in Escherichia coli (JM109-DE3). Since the expressed protein was constructed such that His-tag was attached to the N-terminus thereof, it was purified with Ni-Agarose gel (QIAGEN). Purification was carried out in accordance with the attached protocols. This chromoprotein was named as Be-G. In the following Example A-3, the property of the purified protein was analyzed.

Example A-3

Property of the Chromoprotein (Be-G)

(1) Analysis of Light-Absorbing Properties

Figure 1:
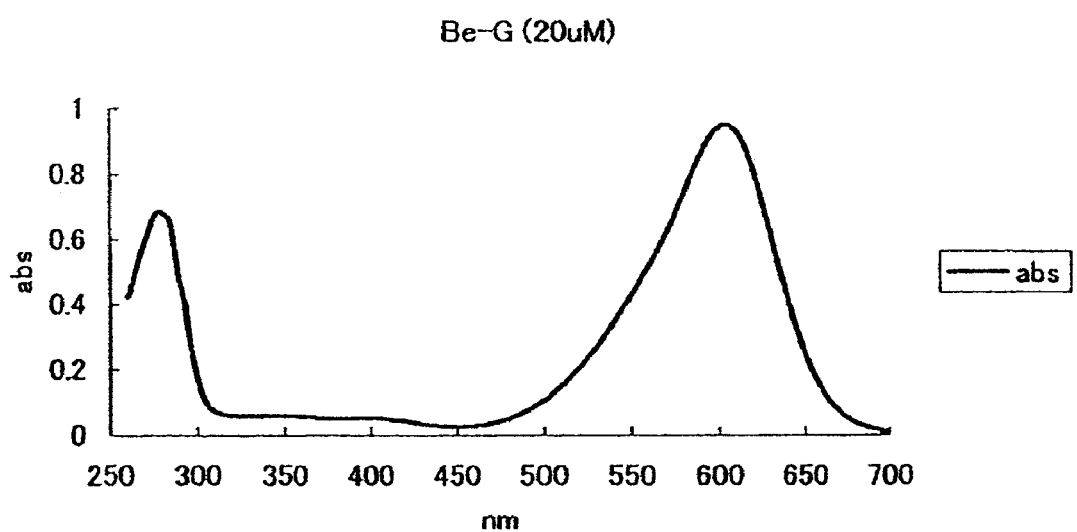
FIG. 1 shows the results obtained by measuring the absorption spectrum of the chromoprotein (Be-G) derived from *Anthopleura inornata* of the present invention. The horizontal axis represents the wavelength of a light absorbed. The longitudinal axis represents absorbance.

An absorption spectrum was measured using a 50 mM HEPES solution (pH 7.9) containing a 20 μM chromoprotein (Be-G). A molar absorption coefficient was calculated from the peak value of this spectrum. In the case of the chromoprotein (Be-G) derived from the green individual, the absorption peak was observed at 605 nm (Table 1, FIG. 1).

TABLE 1

| | Absorption maximum | Fluorescence maximum | Molar absorption coefficient | quantum yield | pH sensitivity | Number of amino acids |
|---|---|---|---|---|---|---|
| Be-G | 605 nm | — | 47,550 (605 nm) | — | None at >pH 5 | 229 |

(2) Measurement of pH Sensitivity

Figure 2:
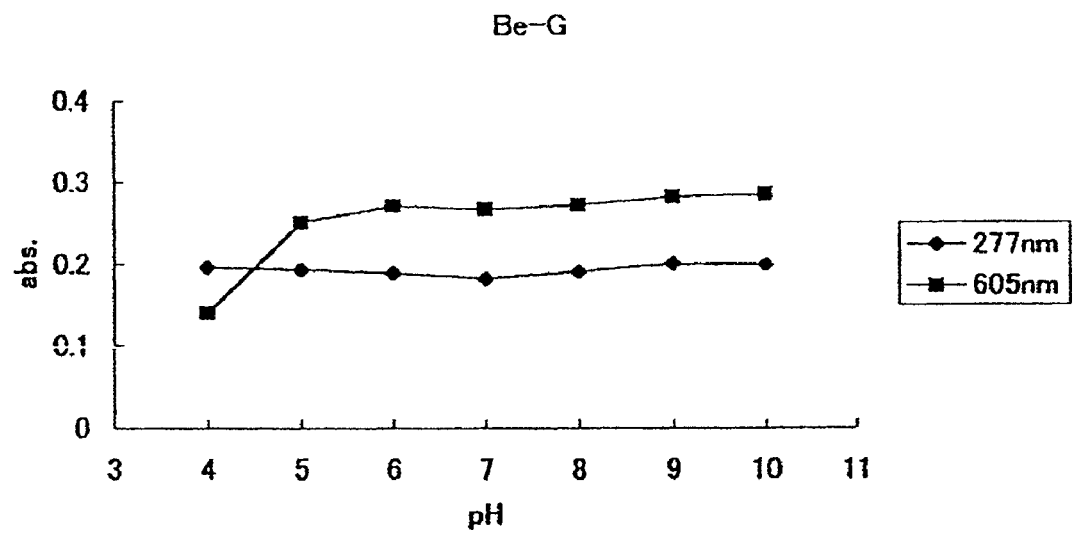
FIG. 2 shows the pH sensitivity of the absorption spectrum of the chromoprotein (Be-G) derived from *Anthopleura inornata* of the present invention. The horizontal axis represents pH value, and the longitudinal axis represents absorbance. 605 nm shows an absorbance specific for the chromoprotein (Be-G) derived from *Anthopleura inornata* of the present invention. 277 nm shows an absorbance that is generally used in quantification of protein (absorbance of aromatic amino acids). That is to say, the value at 277 nm shows that the protein mass is constant, and the value at 605 nm shows that the absorbance specific for the chromoprotein (Be-G) derived from *Anthopleura inornata* of the present invention hardly changes in the range between pH 5 and pH 10.

The absorption spectrum of the protein was measured in the following 50 mM buffer solution (FIG. 2).

The following buffer solutions were used for each pH:
pH 4 and 5: Acetate buffer
pH 6: Phosphate buffer
pH 7 and 8: HEPES buffer
pH 9 and 10: Glycine buffer As is understood from the results of FIG. 2, the peak value was stable at pH 5 to 10.

Example B-1

Isolation of Gene Encoding Novel Chromoprotein from Sea Anemone (1) Extraction of Total RNA A chromoprotein gene was isolated from sea anemone. One individual of Anthopleura inornata emitting a red color was used as a material. Frozen Anthopleura inornata was crushed in a mortar. 7.5 ml of "TRIzol" (GIBCO BRL) was added to 1 g (wet weight) of Anthopleura inornata, and the mixture was homogenized, followed by centrifugation at 1,500×g for 10 minutes. 1.5 ml of chloroform was added to the supernatant. The mixture was stirred for 15 seconds and then left at rest for 3 minutes. The resultant product was centrifuged at 7,500×g for 15 minutes. 3.75 ml of isopropanol was added to the supernatant. The mixture was stirred for 15 seconds and then left at rest for 10 minutes. The resultant product was centrifuged at 17,000×g for 10 minutes. The supernatant was discarded, and 6 ml of 70% ethanol was added thereto. The obtained mixture was centrifuged at 17,000×g for 10 minutes. The supernatant was discarded, and the precipitate was dissolved in 200 l of DEPC water. Total RNA dissolved in the DEPC water was 100 times diluted, and the values of O.D.260 and O.D.280 were measured, so as to determine the concentration of RNA. 3 mg of the total RNA was obtained.

(2) Synthesis of First Stand cDNA cDNA (33 μl) was synthesized from 4 μg of the total RNA using a kit for synthesizing first strand cDNA, "Ready To Go" (Amersham Pharmacia).

(3) Degenerated PCR

Using 3 μl out of the synthesized first strand cDNA (33 μl) as a template, PCR was carried out. Primers were designed and produced by comparing the amino acid sequences of known fluorescent proteins, extracting similar portions, and converting them into nucleotide sequences. The sequences of the used primers are shown below:

```
                                              (SEQ ID NO: 19)
5'-GAAGGRTGYGTCAAYGGRCAY-3'  (primer1)

(SEQ ID NO: 20)
5'-ACVGGDCCATYDGVAAGAAARTT-3'  (primer2)
``` wherein R represents A or G, Y represents C or T, V represents A, C or G, and D represents A, G or T.

| Composition of PCR reaction solution | |
|---|---|
| Template (first strand cDNA) | 3 μl |
| ×10 taq buffer | 5 μl |
| 2.5 mM dNTPs | 4 μl |
| 100 uM primer 1 | 1 μl |
| 100 uM primer 2 | 1 μl |
| Milli Q | 35 μl |
| Taq polymerase (5 U/μl) | 1 μl |
| RCR reaction conditions | |
| 94° C., | 1 minute (PAD) |
| 94° C., | 30 seconds (denaturation) |
| 52° C., | 30 seconds (annealing of the primers to the template) |
| 72° C., | 1 minute (elongation of the primers) |

30 cycles consisting of the above 3 steps were carried out. The annealing temperature was decreased 0.3° C. per cycle. That is to say, the annealing temperature in the 30$^{th}$ cycle was 43° C.
72° C., 7 minutes (final elongation)
Retention at 4° C.

Using 1 μl of an amplified product obtained as a result of the first PCR reaction as a template, PCR was carried out once again under the same conditions. A 350-bp fragment was cut out by agarose gel electrophoresis and then purified.

(4) Subcloning and Sequencing

The purified DNA fragment was ligated to a pT7-blue vector (Novagen). *Escherichia coli* (TG1) was transformed with the vector, and the obtained transformants were subjected to blue white selection. Thereafter, plasmid DNA was purified from white colonies of *Escherichia coli*. The nucleotide sequence of the inserted DNA fragment was determined by a DNA sequencer. The obtained nucleotide sequence was compared with the nucleotide sequences of other fluorescent protein genes to confirm that the nucleotide sequence of the DNA was derived from a fluorescent protein. 5'-RACE and 3'-RACE methods were applied to a gene that had been confirmed to be a part of a fluorescent protein gene, so as to carry out the cloning of a full-length gene.

(5) 5'-RACE Method

In order to determine the nucleotide sequence of the 5'-terminal side of the DNA fragment obtained by degenerated PCR, the 5'-RACE method was applied using 5'-RACE System for Rapid Amplification of cDNA Ends, Version 2.0 (GIBCO BRL). 4 μg of the total RNA prepared in (1) above was used as a template.

For the first amplification of DC-tailed cDNA of the red individual, the following primers were used:

```
                                              (SEQ ID NO: 21)
5'-ggccacgcgtcgactagtacggggnngggnngggnng-3'
(primer3)

(SEQ ID NO: 22)
5'-AAGAGACTCCTTGAAGTAATCGGGA-3'  (primer4)
``` wherein n represents inosine.

For the second amplification, the following primers were used:

```
                                              (SEQ ID NO: 23)
5'-ggccacgcgtcgactagtac-3'  (primer5)

(SEQ ID NO: 24)
5'-AAAATATCGTACGCAAAGGG-3'  (primer6)
```

PCR reaction conditions and the like were determined in accordance with the protocols attached with the kit.

The 200-bp amplified band was cut out by agarose gel electrophoresis and then purified. The purified DNA fragment was ligated to a pT7-blue vector (Novagen). *Escherichia coli* (TG1) was transformed with the vector, and the obtained transformants were subjected to blue white selection. Thereafter, plasmid DNA was purified from white colonies of *Escherichia coli*. The nucleotide sequence of the inserted DNA fragment was determined by a DNA sequencer.

(6) 3'-RACE Method

The 3'-terminal portion of the DNA fragment obtained by degenerated PCR was obtained by PCR, using the primer produced based on the information obtained by sequencing of the nucleotide sequence in (4) above and an oligo dT primer. 3 μl of the first strand cDNA prepared in (2) above was used as a template. The produced primer is shown below:

```
                                              (SEQ ID NO: 25)
5'-AGGAGGTCCGCTACCCTTTG-3'  (primer7)
```

| Composition of PCR reaction solution | |
|---|---|
| Template (first strand cDNA) | 3 μl |
| ×10 taq buffer | 5 μl |
| 2.5 mM dNTPs | 4 μl |
| 20 μM primer 7 | 1 μl |
| 10 μM oligo dT primer | 1 μl |
| Milli Q | 35 μl |
| Taq polymerase (5 U/μl) | 1 μl |
| RCR reaction conditions | |
| 94° C., | 1 minute (PAD) |
| 94° C., | 30 seconds (denaturation) |
| 52° C., | 30 seconds (annealing of the primers to the template) |
| 72° C., | 1 minute (elongation of the primers) |
| 30 cycles consisting of the above 3 steps were carried out. | |
| 72° C., | 7 minutes (final elongation) |
| Retention at 4° C. | |

An amplified band of approximately 1,000 bp was cut out by agarose gel electrophoresis and then purified. The purified DNA fragment was ligated to a pT7-blue vector (Novagen). *Escherichia coli* (TG1) was transformed with the vector, and the obtained transformants were subjected to blue white selection. Thereafter, plasmid DNA was purified from white colonies of *Escherichia coli*. The nucleotide sequence of the inserted DNA fragment was determined by a DNA sequencer. The obtained full-length nucleotide sequence is shown in SEQ ID NO: 4, and the obtained full-length amino acid sequence is shown in SEQ ID NO: 3.

Example B-2

Expression of Protein in *Escherichia coli*

A primer corresponding to the N-terminal of the protein was produced from the obtained full-length nucleotide sequence, and an oligo dT primer was used for C-terminal.

PCR was carried out using these primers and the first strand cDNA prepared in Example B-1 (2) as a template. The used primers are as follows:

```
                                               (SEQ ID NO: 26)
5'-CCCGGATCCGACCATGGCTACCTTGGTTAAAGA-3' (primer8)
```

| Composition of PCR reaction solution | |
|---|---|
| Template (first strand cDNA) | 3 μl |
| x10 pyrobest buffer | 5 μl |
| 2.5 mM dNTPs | 4 μl |
| 100 μM primer 8 | 1 μl |
| 100 μM oligo dT primer | 1 μl |
| Milli Q | 35 μl |
| Pyrobest polymerase (5 U/μl) | 1 μl |

| RCR reaction conditions | |
|---|---|
| 94° C., | 1 minute (PAD) |
| 94° C., | 30 seconds (denaturation) |
| 52° C., | 30 seconds (annealing of the primers to the template) |
| 72° C., | 1 minute (elongation of the primers) |
| 30 cycles consisting of the above 3 steps were carried out. | |
| 72° C., | 7 minutes (final elongation) |
| Retention at 4° C. | |

An amplified band of approximately 1100 bp was cut out by agarose gel electrophoresis and then purified. The purified DNA fragment was subcloned into the BamHI-EcoRI site of a pRSET vector (Invitrogen), and it was then allowed to express in *Escherichia coli* (JM109-DE3). Since the expressed protein was constructed such that His-tag was attached to the N-terminus thereof, it was purified with Ni-Agarose gel (QIAGEN). Purification was carried out in accordance with the attached protocols. This chromoprotein was named as Be-R. In the following Example B-3, the property of the purified protein was analyzed.

Example B-3

Property of the Chromoprotein (Be-R)

(1) Analysis of Light-Absorbing Properties

Figure 3:
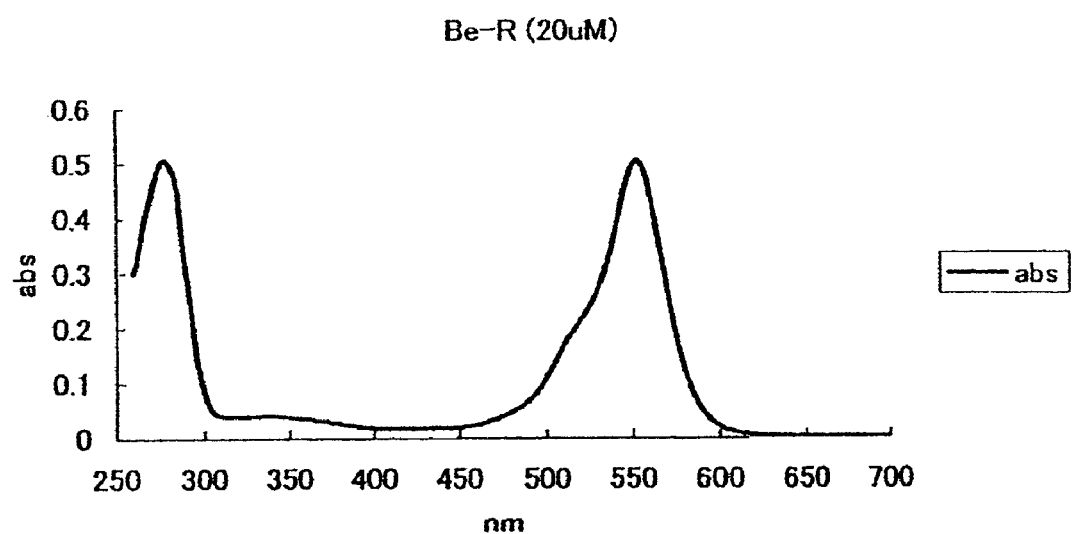
FIG. 3 shows the results obtained by measuring the absorption spectrum of the chromoprotein (Be-R) derived from *Anthopleura inornata* of the present invention. The horizontal axis represents the wavelength of a light absorbed. The longitudinal axis represents absorbance.

An absorption spectrum was measured using a 50 mM HEPES solution (pH 7.9) containing a 20 μM chromoprotein. A molar absorption coefficient was calculated from the peak value of this spectrum. In the case of the chromoprotein (Be-R) derived from the red individual, the absorption peak was observed at 553 nm (Table 2, FIG. 3).

TABLE 2

| | Absorption maximum | Fluorescence maximum | Molar absorption coefficient | quantum yield | pH sensitivity | Number of amino acids |
|---|---|---|---|---|---|---|
| Be-R | 553 nm | — | 25,300 (553 nm) | — | None at >pH 5 | 229 |

(2) Measurement of pH Sensitivity

Figure 4:
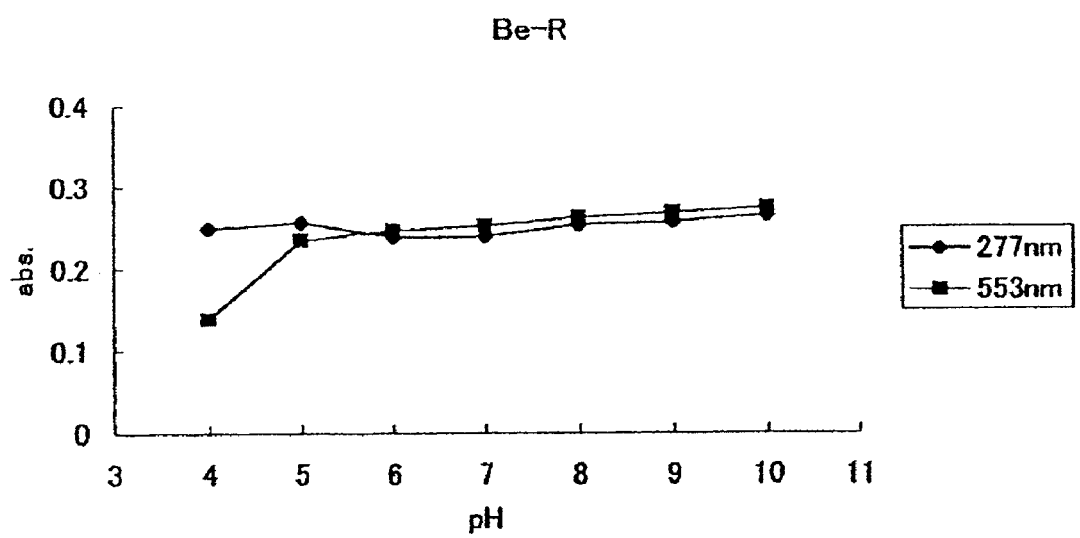
FIG. 4 shows the pH sensitivity of the absorption spectrum of the chromoprotein (Be-R) derived from *Anthopleura inornata* of the present invention. The horizontal axis represents pH value, and the longitudinal axis represents absorbance. 553 nm shows an absorbance specific for the chromoprotein (Be-R) derived from *Anthopleura inornata* of the present invention. 277 nm shows an absorbance that is generally used in quantification of protein (absorbance of aromatic amino acids). That is to say, the value at 277 nm shows that the protein mass is constant, and the value at 553 nm shows that the absorbance specific for the chromoprotein (Be-R) derived from *Anthopleura inornata* of the present invention hardly changes in the range between pH 5 and pH 10.

The absorption spectrum of the protein was measured in the following 50 mM buffer solution (FIG. 4).

The following buffer solutions were used for each pH:
pH 4 and 5: Acetate buffer
pH 6: Phosphate buffer
pH 7 and 8: HEPES buffer
pH 9 and 10: Glycine buffer As is understood from the results of FIG. 4, the peak value was stable at pH 5 to 10.

Example C-1

Isolation of Novel Fluorescent Protein Gene (Kaede) from Coral

A fluorescent protein gene was isolated from *Trachyphyllia geoffroyi* which emits fluorescence with rich colors by the following procedures.

(1) Extraction of Total RNA

Total RNA was extracted by acidic guanidium/phenol/chloroform method.

Frozen *Trachyphyllia geoffroyi* was crushed in a denaturation solution by using a Multi-Beads Shocker (Yasui Kikai), and then phenol/chloroform was added thereto, followed by centrifugation to separate RNA from protein and DNA. A water phase containing RNA was added to isopropanol, and the mixture was centrifuged, so as to obtain total RNA as a precipitate.

(2) Purification of RNA

Using Oligotex-dT30 (manufactured by Roche), mRNA was separated from the total RNA.

Oligotex-dT30<super> was added to the total RNA, and the mixture was then heated, so as to destroy the secondary structure of the RNA. Thereafter, the RNA was bound to Oligotex-dT at 37° C. After washing, the resultant product was heated and centrifuged, so as to obtain a supernatant eluted from the mRNA. Oligotex-dt was eliminated from the supernatant, and then, mRNA was allowed be precipitated with ethanol and NaCl. The mRNA was then dissolved in water.

(3) Preparation of cDNA

A cDNA fragment was prepared using TimeSaver and Directional Cloning Toolbox (both of which were manufactured by Amersham Pharmacia).

The mRNA was heated to destroy the secondary structure thereof. Thereafter, the mRNA, DTT, and a NotI-dT primer were added to First-Strand Reaction Mix, so as to synthesize a first strand. This was then added to Second-Strand Reaction Mix, so as to synthesize a second strand. The synthesized second strand was purified with a span column attached with the kit. EcoRI adaptors were added to both termini of the purified double-stranded cDNA, and only the 3'-side thereof was cleaved with NotI. It was purified again with the span column, so as to obtain a cDNA fragment (EcoRI-NotI).

(4) Expression Cloning

An EcoRI-NotI site was made in pRSETB (manufactured by Invitrogen), and the prepared cDNA was inserted into the site. Thereafter, the thus prepared vector was introduced into *Escherichia coli* JM109 DM3, followed by culture on an LA plate. Since a protein is synthesized in this strain, colonies that emit fluorescence when UV is applied were isolated.

As a result, 2 colonies emitting fluorescence were obtained from approximately 130,000 colonies. The nucleotide sequence thereof was determined with a DNA sequencer. This clone was named as Kaede. The amino acid sequence of Kaede is shown in SEQ ID NO: 5 of the sequence listing, and the nucleotide sequence of Kaede is shown in SEQ ID NO: 6.

(5) Analysis of Fluorescence Properties (a) Expression and Purification of Protein A BamHI site was added to the N-terminus of the obtained full-length cDNA, and an EcoRI site was added to the C-terminus thereof. Thereafter, it was subcloned in frame into pRSETB (manufactured by Invitrogen), and it was then expressed in *Escherichia coli* JM109 DE3. The expressed protein was purified with Ni-Agarose gel (manufactured by QIAGEN), utilizing an His-tag at the N-terminus thereof.

Figure 5:
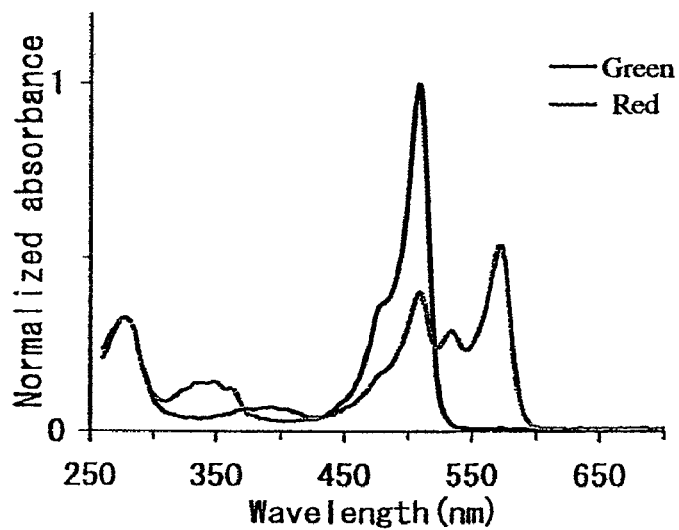
FIG. 5 is the absorption spectrum of the fluorescent protein (Kaede) of the present invention.

(b) Absorption Spectrum and Molar Absorption Coefficient, and Fluorescence Spectrum and Quantum Yield When this fluorescent protein is irradiated with UV, the absorption and fluorescence spectra thereof shift to long wavelengths, from green to red. FIG. 5 shows the absorption spectrum of a purified protein before and after UV irradiation (the solid line represents the absorption spectrum before UV irradiation, and the dotted line represents the absorption spectrum after UV irradiation). The molar absorption coefficient was obtained from the concentration of the protein and the absorbance at absorption maximum (Table 3).

Figure 6:
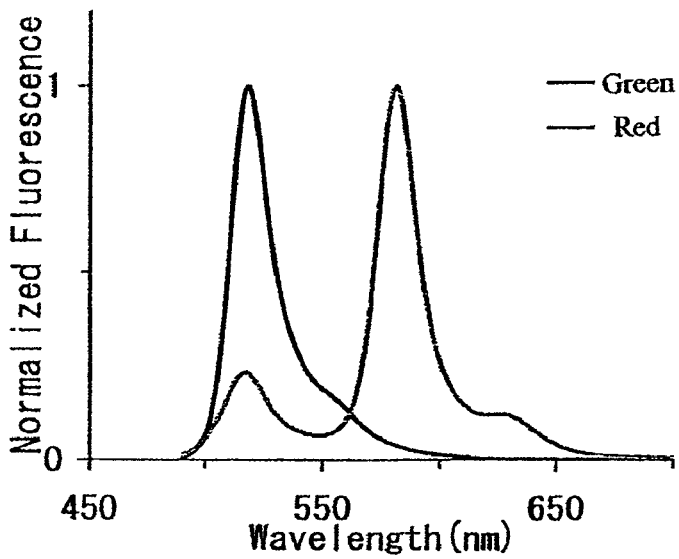
FIG. 6 is the fluorescence spectrum of the fluorescent protein (Kaede) of the present invention.

The fluorescence spectrum was measured by exciting the protein at 480 nm before and after UV irradiation (FIG. 6), and the quantum yield was calculated by comparison with Fluorescein (manufactured by Molecular Probes) (Table 3).

The fluorescence properties of Kaede are shown in the following Table 3.

(c) Properties Regarding pH Sensitivity

The absorption spectra of green and red were measured in a buffer each having pH 4 to 11. In both cases of green and red, the absorption level gradually decreases on reaching pH 9. pKa calculated from a change in the absorption maximum is shown in the above Table 3.

Example C-2

Introduction of Novel Fluorescent Protein Gene into Mammalian Cells

Figure 7:
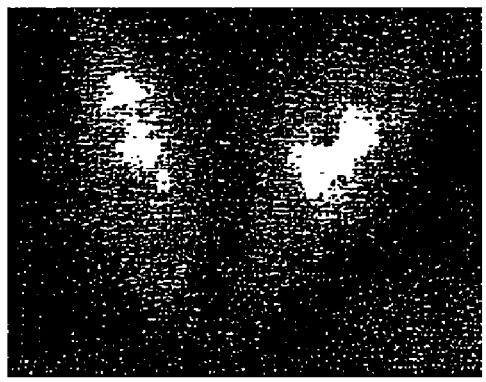
FIG. 7 shows the results obtained by exciting at 470 nm, HeLa cells into which the gene of the fluorescent protein (Kaede) of the present invention has been introduced, and measuring them with the fluorescence at 510 nm.

The Kaede gene was introduced into HeLa cells, using LIPOFECTIN Reagent (Gibco). FIG. 7 shows the results obtained by exciting the cells at 470 nm and measuring them with the fluorescence at 510 nm. Fluorescence can be confirmed approximately 9 hours after the introduction. Fluorescence shifts to a long wavelength even in mammalian cells, when the cells are irradiated with UV.

Example C-3

Dimerization of Kaede

Figure 8:
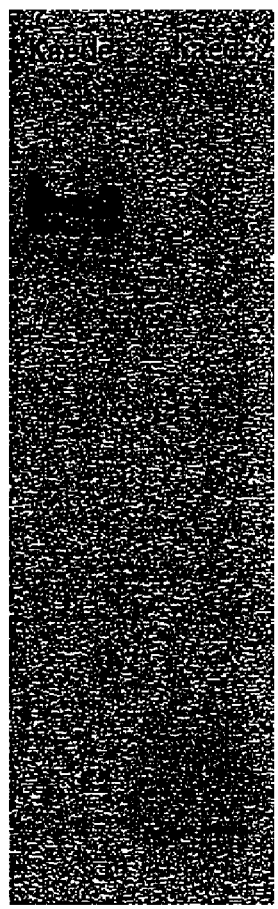
FIG. 8 is the electrophoretic patterns of Kaede and Kaede 2 in 12.5% acrylamide. Kaede 2 band appears as one having a lower molecular weight than that of Kaede.
Figure 9:
FIG. 9 is an expression pattern obtained when Kaede (upper figure) and Kaede 2 (lower figure) were targeted to the plasma membrane of HeLa cells.
Figure 9:

Since Kaede forms a tetramer, there may be cases where its expression pattern becomes abnormal when another protein is fused with Kaede. Thus, in Kaede, threonine (T) at position 158 was substituted with arginine (R), and alanine (A) at position 160 was substituted with glutamic acid (E), so as to produce a dimeric mutant. This mutant was named as Kaede 2. The amino acid sequence and nucleotide sequence of Kaede 2 are shown in SEQ ID NOS: 7 and 8 in the sequence listing, respectively. In electrophoresis on 12.5% acrylamide gel where sample was not boiled (Pseudonative SDS/PAGE), a band of Kaede 2 was detected as a molecule with a lower molecular weight than that of Kaede (FIG. 8). In addition, when Kaede and Kaede 2 were allowed to express in the plasma membrane of HeLa cells, Kaede exhibited an apparently abnormal expression pattern. However, Kaede 2 exhibited a normal expression pattern showing that it was properly targeted into the plasma membrane (FIG. 9).

Example C-4

Ultraviolet Ray Irradiation-Dependent Cleavage of Kaede Protein

Change in the fluorescence properties of Kaede from green to red by means of irradiation with ultraviolet rays involves the cleavage of the protein. The results from 12.5% acrylamide gel electrophoresis show that 27 kDa Kaede molecule is cleaved into a 17 kDa peptide chain and a 10 kDa peptide chain by irradiation with light at 365 nm (the upper column in FIG. 10). The results also show that the absorption value at

TABLE 3

Fluorescence properties of Kaede

| Excitation maximum (nm) | Fluorescence maximum (nm) | Molar absorption coefficient ($M^{-1}/cm^{-1}$) | Quantum yield | pH sensitivity (pKa) | Number of amino acids |
|---|---|---|---|---|---|
| Green: 508 nm<br>Red: 572 nm | Green: 518 nm<br>Red: 581 nm | Green: 98,800 (508 nm)<br>Red: 60,400 (572 nm) | Green: 0.80<br>Red: 0.33 | Green: 5.7<br>Red: 5.7 | 225 |

Figure 10:
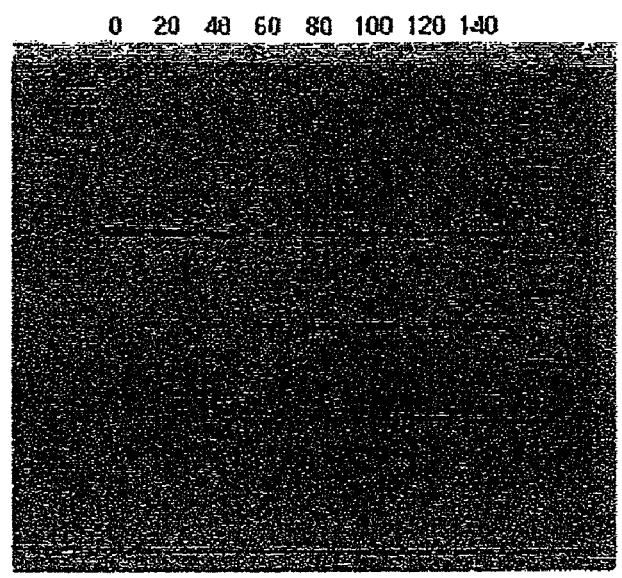
FIG. 10 shows the experimental results showing the ultraviolet ray-irradiation-dependent cleavage of a Kaede protein. The upper figure shows a transition in the ultraviolet ray-irradiation-dependent cleavage of a peptide chain in the form of an electropherogram on 12.5% acrylamide gel. A Kaede protein solution was irradiated with light at 365 nm, sampling was conducted every 20 minutes, and SDS/PAGE was carried out. The middle figure shows the absorption spectrum observed before irradiation with light at 365 nm (0 minute). The lower figure shows the absorption spectrum observed 140 minutes after irradiation with light at 365 nm.
Figure 10:
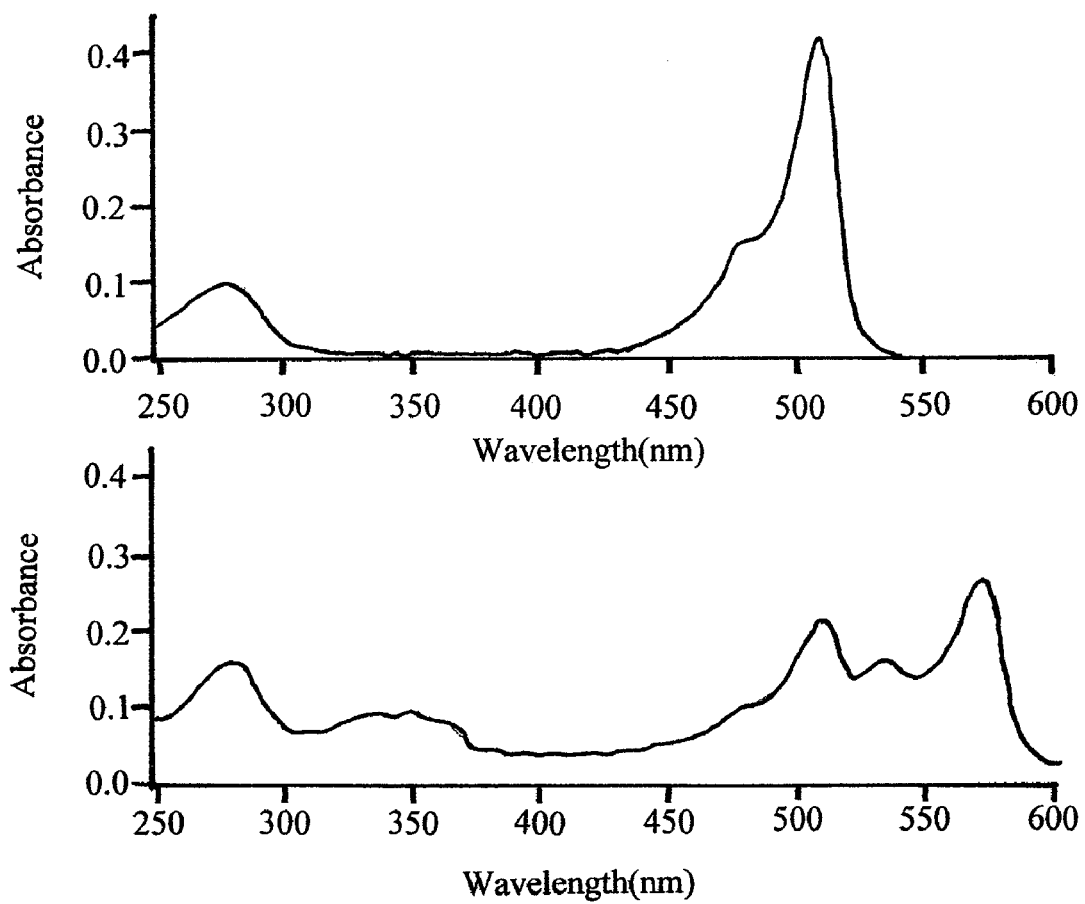

508 nm is reduced and the absorption value at 572 nm is increased by irradiation with light at 365 nm, thereby indicating that the fluorescence properties are changed from green to red (the middle and lower columns in FIG. 10). Such properties can be used for a technique of controlling the cleavage of a protein by light. A technique of cleaving a protein by light has not yet been reported. Moreover, such a cleavage is associated with a β-elimination reaction in a protein. However, such a β-elimination reaction in a protein, or a β-elimination reaction in which an amide group acts as a leaving group, has not yet been reported.

Example D-1

Isolation of Novel Fluorescent Protein Gene from Coral (1) Extraction of Total RNA A fluorescent protein gene was isolated from coral emitting fluorescence. *Scolymia vitiensis* was used as a material. *Scolymia vitiensis* was crushed by hammer, and 15 ml of "TRIzol" (GIBCO BRL) was added to 10 g of the crushed coral, and the mixture was stirred, followed by centrifugation at 1,500×g for 10 minutes. 3 ml of chloroform was added to the supernatant. The mixture was stirred for 15 seconds and then left at rest for 3 minutes. The resultant product was centrifuged at 7,500×g for 15 minutes. 7.5 ml of isopropanol was added to the supernatant. The mixture was stirred for 15 seconds and then left at rest for 10 minutes. The resultant product was centrifuged at 17,000×g for 10 minutes. The supernatant was discarded, and 6 ml of 70% ethanol was added thereto. The obtained mixture was centrifuged at 17,000×g for 10 minutes. The supernatant was discarded, and the precipitate was dissolved in 200 μl of DEPC water. Total RNA dissolved in the DEPC water was 100 times diluted, and the values of O.D.260 and O.D.280 were measured, so as to determine the concentration of RNA. 230 μg of the total RNA was obtained.

(2) Synthesis of First Stand cDNA cDNA (33 μl) was synthesized from 3 μg of the total RNA using a kit for synthesizing first strand cDNA, "Ready To Go" (Amersham Pharmacia).

(3) Degenerated PCR

Using 3 μl out of the synthesized first strand cDNA (33 μl) as a template, PCR was carried out. Primers were designed and produced by comparing the amino acid sequences of known fluorescent proteins, extracting similar portions, and converting them into nucleotide sequences. The sequences of the used primers are shown below:

```
                                      (SEQ ID NO: 27)
5'-ATCAAGNTNWRYATGGAAGG-3' (primer1)

(SEQ ID NO: 28)
5'-acVggDccatYDgVaagaaaRtt-3' (primer2)
``` wherein R represents A or G, Y represents C or T, V represents A, C or G, D represents A, G or T, and N represents A, G, C, or T.

| Composition of PCR reaction solution | |
|---|---|
| Template (first strand cDNA) | 3 μl |
| ×10 taq buffer | 5 μl |
| 2.5 mM dNTPs | 4 μl |
| 100 uM primer 1 | 1 μl |

-continued

| | |
|---|---|
| 100 uM primer 2 | 1 μl |
| Milli Q | 35 μl |
| Taq polymerase (5 U/μl) | 1 μl |

| RCR reaction conditions | |
|---|---|
| 94° C., | 1 minute (PAD) |
| 94° C., | 30 seconds (denaturation) |
| 52° C., | 30 seconds (annealing of the primers to the template) |
| 72° C., | 1 minute (elongation of the primers) |
| 30 cycles consisting of the above 3 steps were carried out. The annealing temperature was decreased 0.3° C. per cycle. That is to say, the annealing temperature in the 30th cycle was 43° C. | |
| 72° C., | 7 minutes (final elongation) |
| Retention at 4° C. | |

Using 1 μl of an amplified product obtained as a result of the first PCR reaction as a template, PCR was carried out once again under the same conditions. A 350-bp fragment was cut out by agarose gel electrophoresis and then purified.

(4) Subcloning and Sequencing

The purified DNA fragment was ligated to pT7-blue vector (Novagen). *Escherichia coli* (TG1) was transformed with the vector, and the obtained transformants were subjected to blue white selection in the presence of X-gal. Thereafter, plasmid DNA was purified from white colonies of *Escherichia coli*. The nucleotide sequence of the inserted DNA fragment was determined by a DNA sequencer. The obtained nucleotide sequence was compared with the nucleotide sequences of other fluorescent protein genes to confirm that the nucleotide sequence of the DNA was derived from a fluorescent protein. 5'-RACE and 3'-RACE methods were applied to a gene that had been confirmed to be a part of a fluorescent protein gene, so as to carry out the cloning of a full-length gene.

(5) 5'-RACE Method

In order to determine the nucleotide sequence of the 5'-terminal side of the DNA fragment obtained by degenerated PCR, the 5'-RACE method was applied using 5'-RACE System for Rapid Amplification of cDNA Ends, Version 2.0 (GIBCO BRL). 3 μg of the total RNA prepared in (1) above was used as a template.

For the first amplification of DC-tailed cDNA, the following primers were used:

```
                                            (SEQ ID NO: 21)
5'-ggccacgcgtcgactagtacgggnngggnngggnng-3'
(primer3)

(SEQ ID NO: 29)
5'-AGTTCACACCATGATATTCAATATCATA-3' (primer4)
``` wherein n represents inosine.

For the second amplification, the following primers were used:

```
                                            (SEQ ID NO: 30)
5'-ggccacgcgtcgactagtac-3' (primer5)

(SEQ ID NO: 31)
5'-TCTTCGTAAGTCATGCTTCGTTC-3' (primer6)
```

PCR reaction conditions and the like were determined in accordance with the protocols attached with the kit.

The 400-bp amplified band was cut out by agarose gel electrophoresis and then purified. The purified DNA fragment was ligated to a pT7-blue vector (Novagen). *Escheri-* chia coli (TG1) was transformed with the vector, and the obtained transformants were subjected to blue white selection in the presence of X-gal. Thereafter, plasmid DNA was purified from white colonies of *Escherichia coli*. The nucleotide sequence of the inserted DNA fragment was determined by a DNA sequencer.

(6) 3'-RACE Method

The 3'-terminal portion of the DNA fragment obtained by degenerated PCR was obtained by PCR, using the primer produced based on the information obtained by sequencing of the nucleotide sequence in (4) above and an oligo dT primer. 3 μl of the first strand cDNA prepared in (2) above was used as a template. The produced primer is shown below:

```
                                    (SEQ ID NO: 32)
5'-GGTATTCGCCAAATACCCAAA-3'  (primer7)
```

| Composition of PCR reaction solution | |
|---|---|
| Template (first strand cDNA) | 3 μl |
| ×10 taq buffer | 5 μl |
| 2.5 mM dNTPs | 4 μl |
| 20 μM primer 7 | 1 μl |
| 10 μM oligo dT primer | 1 μl |
| Milli Q | 35 μl |
| Taq polymerase (5 U/μl) | 1 μl |
| RCR reaction conditions | |
| 94° C., 1 minute (PAD) | |
| 94° C., 30 seconds (denaturation) | |
| 52° C., 30 seconds (annealing of the primers to the template) | |
| 72° C., 1 minute (elongation of the primers) | |
| 30 cycles consisting of the above 3 steps were carried out. | |
| 72° C., 7 minutes (final elongation) | |
| Retention at 4° C. | |

An amplified band of approximately 500 bp was cut out by agarose gel electrophoresis and then purified. The purified DNA fragment was ligated to a pT7-blue vector (Novagen). *Escherichia coli* (TG1) was transformed with the vector, and the obtained transformants were subjected to blue white selection in the presence of X-gal. Thereafter, plasmid DNA was purified from white colonies of *Escherichia coli*. The nucleotide sequence of the inserted DNA fragment was determined by a DNA sequencer.

(7) Obtainment of Full-Length cDNA

An open reading frame encoding a fluorescent protein was determined based on the obtained full-length nucleotide sequence. Primers were produced from portions corresponding to the N-terminus and the C-terminus. PCR was carried out using the First strand cDNA prepared in (2) above as a template, so as to obtain full-length cDNA. This clone was named as Momiji. The amino acid sequence of Momiji is shown in SEQ ID NO: 9, and the nucleotide sequence thereof is shown in SEQ ID NO: 10.

The primers used are shown below:

```
                                            (SEQ ID NO: 33)
5'-CCCGGATCCGACCATGGTGAGTGTGATTAAGGACGAAATG-3'
(primer8)

(SEQ ID NO: 34)
5'-CCGCTCGAGTTGTTGTTGTTTCTCTTTGTCCTG-3' (primer9)
```

| Composition of PCR reaction solution | |
|---|---|
| Template (first strand cDNA) | 3 μl |
| ×10 taq buffer | 5 μl |
| 2.5 mM dNTPs | 4 μl |
| 20 μM primer 4 | 1 μl |
| 20 μM primer 5 | 1 μl |
| Milli Q | 35 μl |
| Taq polymerase (5 U/μl) | 1 μl |
| RCR reaction conditions | |
| 94° C., 1 minute (PAD) | |
| 94° C., 30 seconds (denaturation) | |
| 52° C., 30 seconds (annealing of the primers to the template) | |
| 72° C., 1 minute (elongation of the primers) | |
| 30 cycles consisting of the above 3 steps were carried out. | |
| 72° C., 7 minutes (final elongation) | |
| Retention at 4° C. | |

Example D-2

Expression of Protein in *Escherichia coli*

A band of 700 bp amplified in Example D-1 (7) was cut out by agarose gel electrophoresis and then purified. The purified DNA fragment was subcloned into the NcoI-XhoI site of a pET28 vector (Novagen), and it was then allowed to express in *Escherichia coli* (JM109-DE3). Since the expressed protein was constructed such that His-tag was attached to the N-terminus thereof, it was purified with Ni-Agarose gel (QIAGEN). Purification was carried out in accordance with the attached protocols. In the following Example D-3, the property of the purified protein (Momiji) was analyzed.

Example D-3

Analysis of Fluorescent Protein (1) Analysis of Fluorescence Properties

Figure 11:
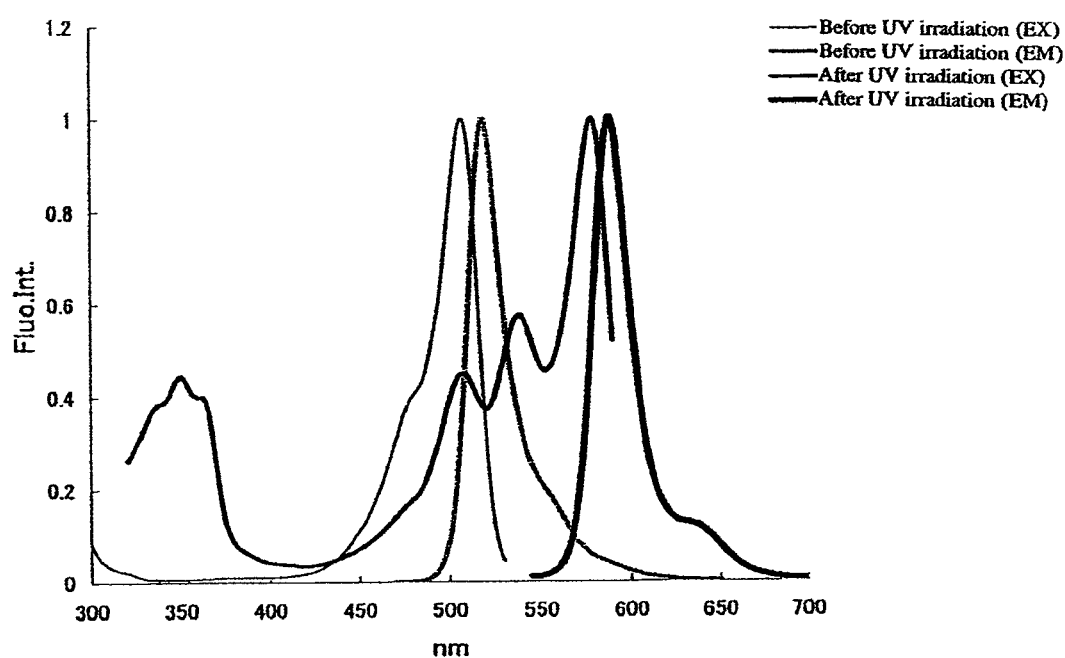
FIG. 11 shows the excitation spectrum and fluorescence spectrum of the fluorescent protein (Momiji) of the present invention.

The absorption spectrum of a solution consisting of a 20 μM fluorescent protein (Momiji), 50 mM HEPES (pH 7.4), and 150 mM KCl was measured. Thereafter, the solution was 20 times diluted with the aforementioned buffer solution, and the fluorescence spectrum and excitation spectrum thereof were measured. Separately, molar absorption coefficients at 508 nm and at 578 nm were calculated based on the protein concentration obtained by the Bradford method and the peak value of the absorption spectrum. The fluorescent protein was diluted with the same above buffer solution such that the absorption at 450 nm became 0.002, and the fluorescence spectrum obtained by excitation at 450 nm was measured. Likewise, EGFP (CLONTECH) was diluted such that the absorption at 450 nm became 0.002, and the fluorescence spectrum was measured. Thereafter, the quantum yield of fluorescence in the cloned fluorescent protein was obtained from the area ratio between both the spectra. The quantum yield of fluorescence in EGFP was set at 0.6. The measurement results are shown in Table 4 and FIG. 11.

TABLE 4

| | Momiji | EGFP |
|---|---|---|
| Excitation maximum | 508 nm, 578 nm | 490 nm |
| Fluorescence maximum | 518 nm, 588 nm | 509 nm |
| Molar absorption coefficient | 102250 (508 nm), 76950 (578 nm) | 48850 (490 nm) |
| Quantum yield (fluorescence) | 0.43 (518 nm), 0.51 (588 nm) | 0.600 |
| pH sensitivity | pKa = 5.8 (508 nm), pKa = 6.5 (578 nm) | pKa = 6.0 |
| Number of amino acids | 229 a.a. | 238 a.a. |

(2) Measurement of Change in Spectrum by UV

Figure 13:
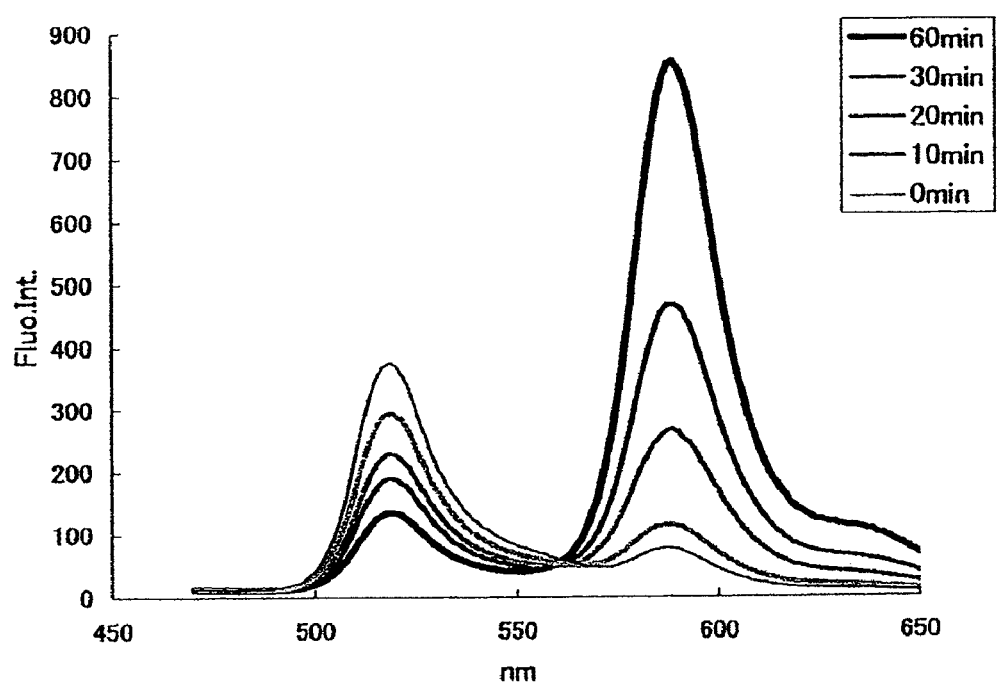
FIG. 13 shows a change in the fluorescence spectrum when the fluorescent protein (Momiji) of the present invention is irradiated with 365 nm UV.
Figure 14:
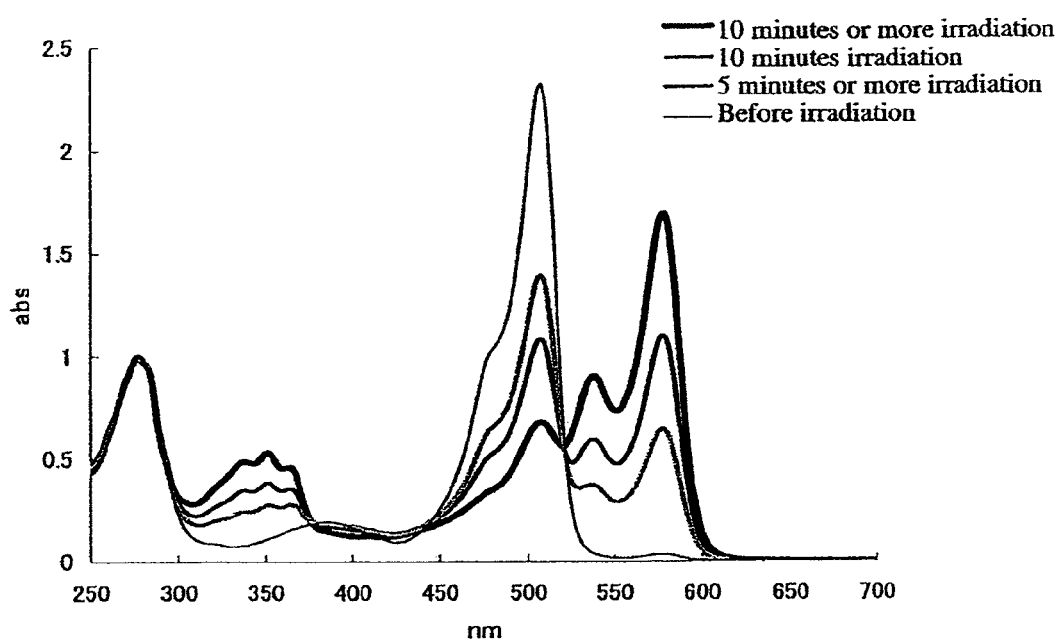
FIG. 14 shows a change in the absorption spectrum when the fluorescent protein (Momiji) of the present invention is irradiated with 365 nm UV.

The fluorescence and absorption spectra of the fluorescent protein (Momiji) of the present invention change by irradiation with UV (around 365 nm). Such changes were measured. The fluorescent protein was diluted with a solution consisting of 50 mM HEPES (pH 7.4) and 150 mM KCl. The diluted solution was irradiated with light at 365 nm, and the fluorescence spectrum obtained by excitation at 365 nm was then measured. In addition, a solution consisting of a 20 µM fluorescent protein, 50 mM HEPES (pH 7.4), and 150 mM KCl was used, and the absorption spectrum thereof was measured after irradiation with light at 365 nm. The measurement results are shown in FIGS. 13 and 14. Since the amount of light at 365 nm was different between the measurement of the fluorescence spectrum and that of the absorption spectrum, change and time in the fluorescent spectrum did not correspond to those in the absorption spectrum.

(3) Measurement of pH Sensitivity

The absorption spectrum was obtained in the buffer solutions of pH 4 to 11, and the pH sensitivity (pKa) was measured.

Figure 12:
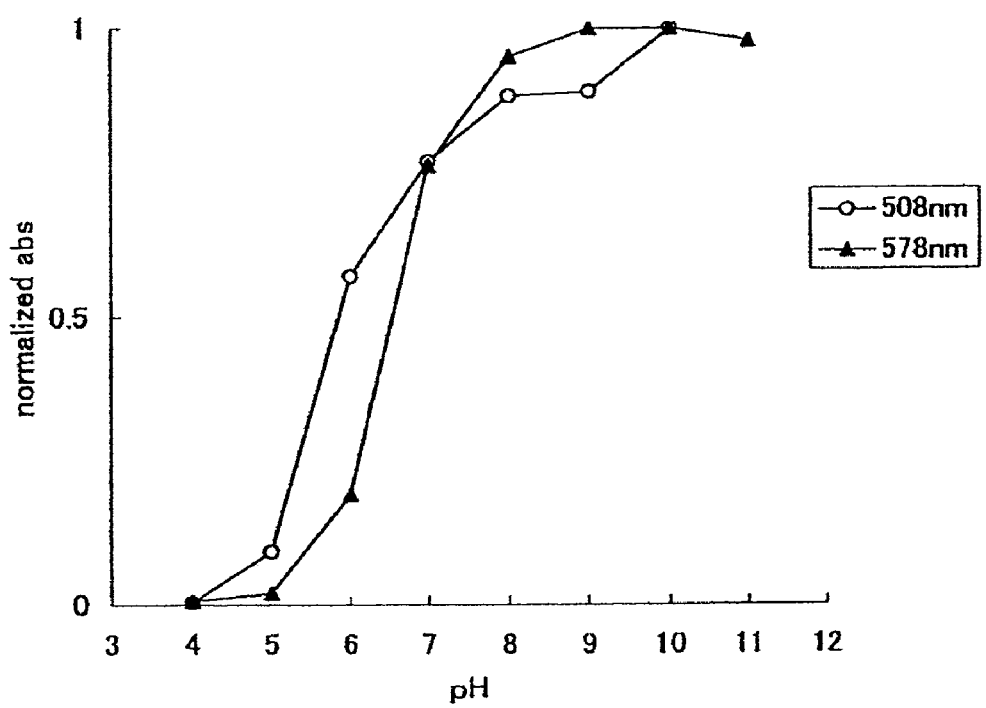
FIG. 12 shows the pH sensitivity of the fluorescent protein (Momiji) of the present invention.

The following buffer solutions were used for each pH:
pH 4 and 5: Acetate buffer
pH 6 and 11: Phosphate buffer
pH 7 and 8: HEPES buffer
pH 9 and 10: Glycine buffer The results of measurements and the like are shown in Table 4 and FIG. 12.

Example D-4

Improvement of Fluorescence Properties of Momiji

Figure 15:
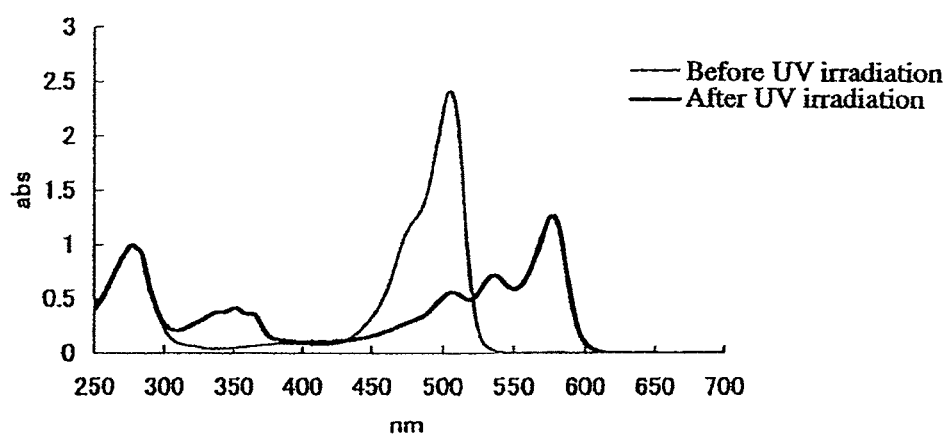
FIG. 15 shows a change in the absorption spectrum before and after irradiation with UV (Momiji 2).
Figure 17:
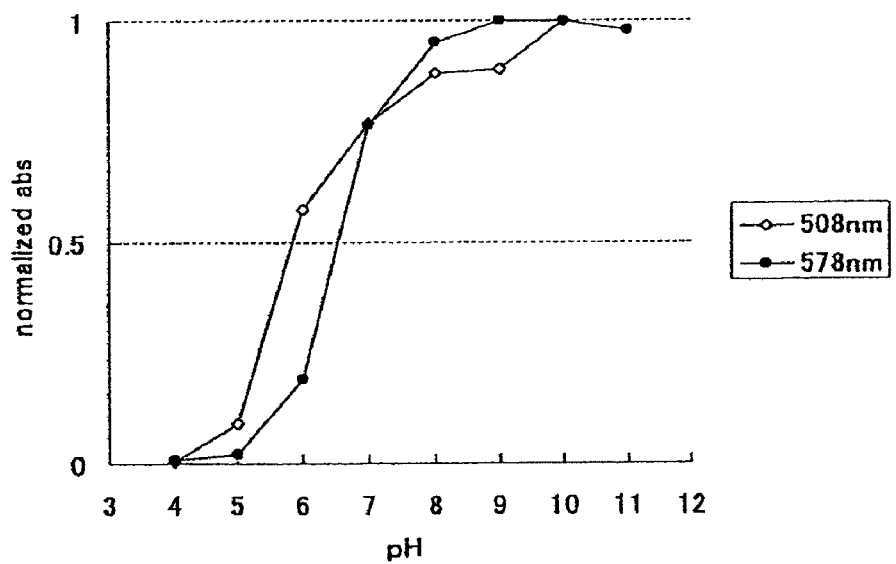
FIG. 17 shows a change in the absorption spectrum due to pH before and after irradiation with UV (Momiji). Before irradiation: 508 nm; and after irradiation: 578 nm.
Figure 18:
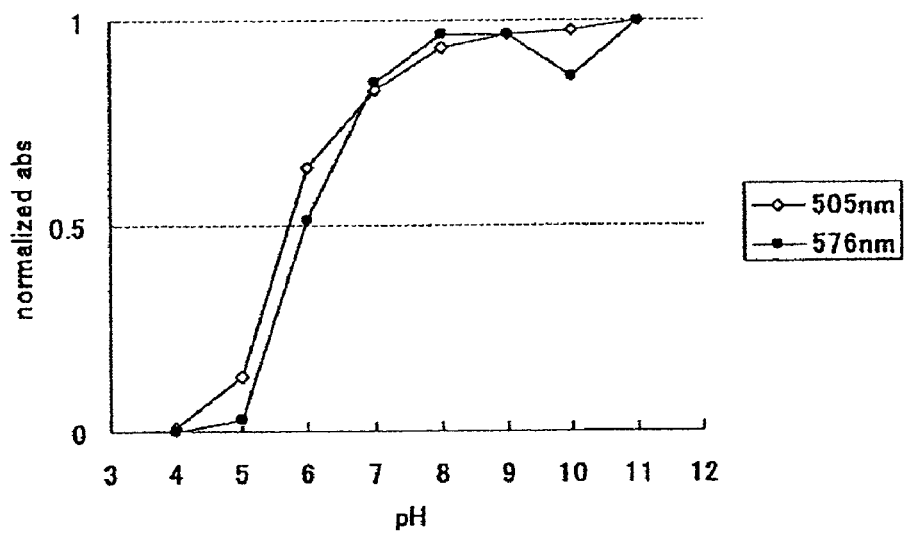
FIG. 18 shows a change in the absorption spectrum due to pH before and after irradiation with UV (Momiji 2). Before irradiation: 508 nm; and after irradiation: 576 nm.
Figure 21:
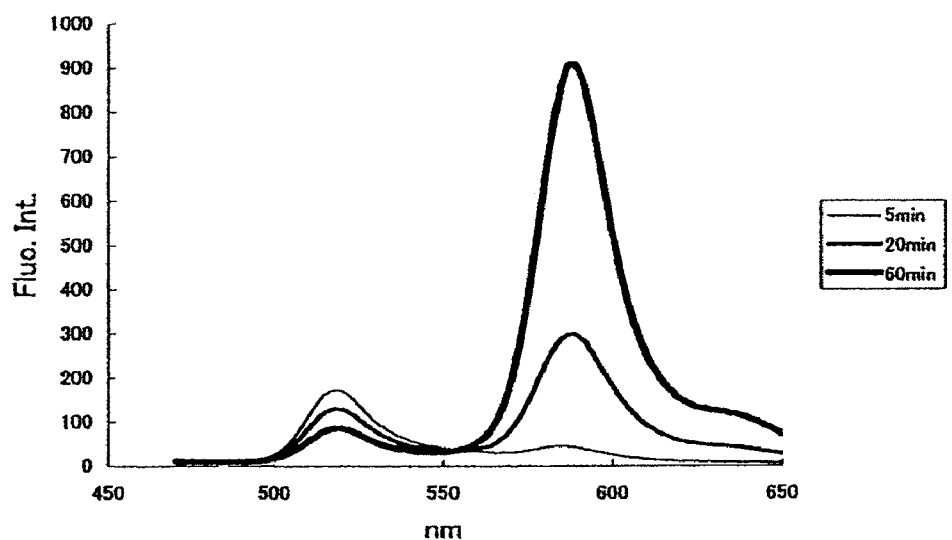
FIG. 21 shows a transition in a change in fluorescence properties depending on irradiation time with light at 365 nm (Momiji 2). Measurement was carried out on a 6 µg/ml protein solution. In order to clearly differentiate the situation from that of a mutant, light exchange was carried out with extremely weak light at 365 nm, and the fluorescence spectrum from 470 nm to 650 nm was measured.

In Momiji, glutamic acid (E) at position 86 was substituted with lysine (K), aspartic acid (D) at position 111 was substituted with glutamic acid (E), glutamine (Q) at position 142 was substituted with proline (P), and arginine (R) at position 203 was substituted with histidine (H). By such substitutions, the molar absorption coefficient increased from 102250 (508 nm) to 127200 (505 nm). Thus, the green fluorescence became brighter, while retaining its fluorescence properties that ultraviolet ray-irradiation-dependently change from green to red (Table 5, and FIGS. 15 and 21). Moreover, the molecule emitting red fluorescence, whose fluorescence properties ultraviolet ray-irradiation-dependently changed, had pH resistivity that was lower than that of the wild type (Momiji) (FIGS. 17 and 18). This mutant was named as Momiji 2. The amino acid sequence and nucleotide sequence of Momiji 2 are shown in SEQ ID NOS: 11 and 12, respectively.

Example D-5

Improvement of Light-Irradiation-Dependent Fluorescence Properties of Momiji

Figure 16:
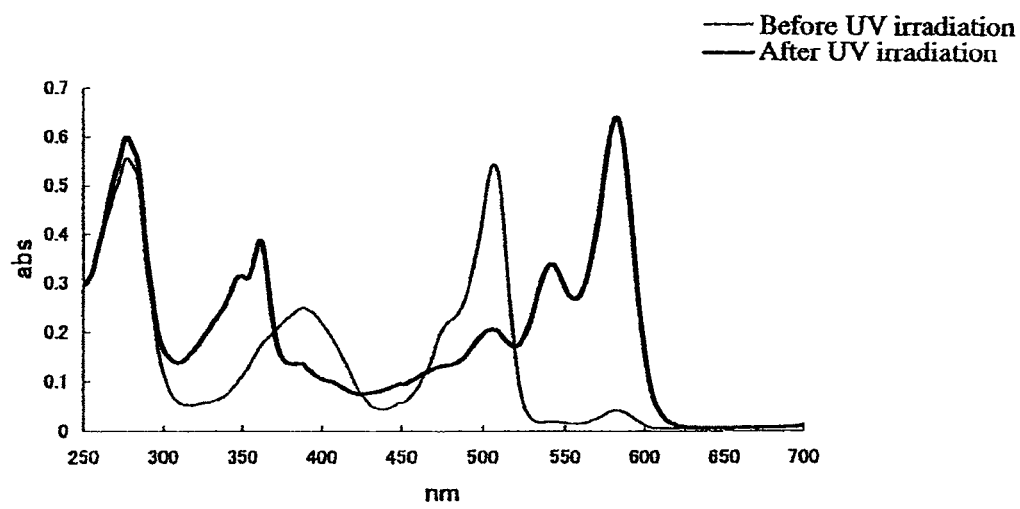
FIG. 16 shows a change in the absorption spectrum before and after irradiation with UV (Momiji 4).
Figure 19:
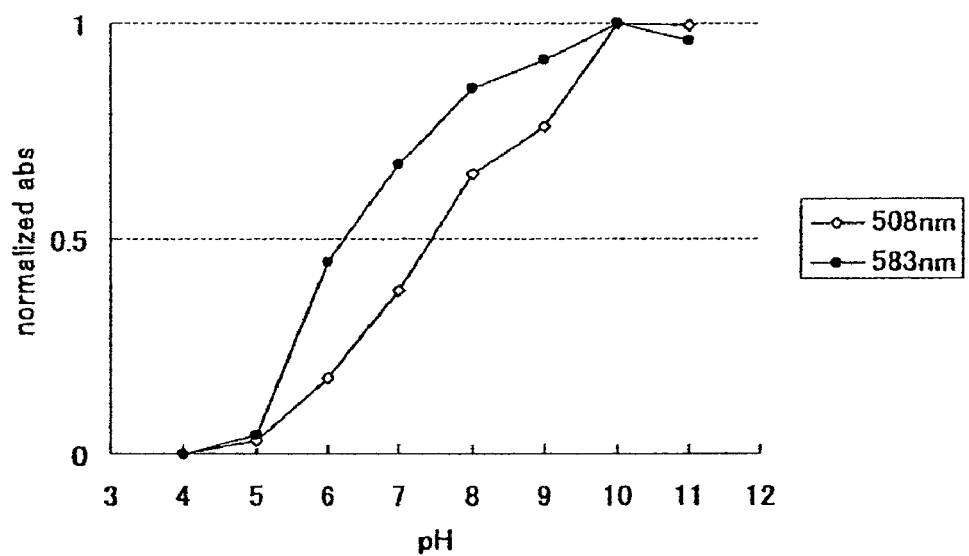
FIG. 19 shows a change in the absorption spectrum due to pH before and after irradiation with UV (Momiji 4). Before irradiation: 508 nm; and after irradiation: 583 nm.
Figure 20:
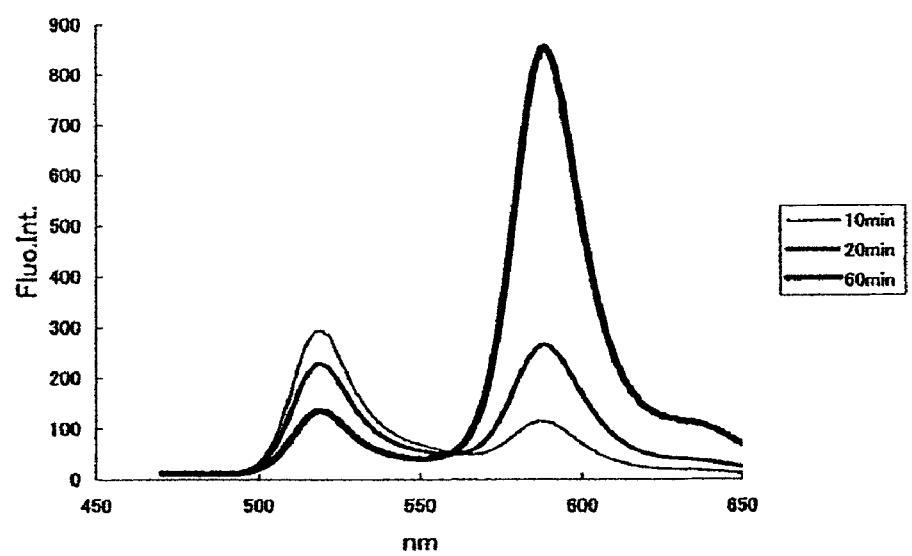
FIG. 20 shows a transition in a change in fluorescence properties depending on irradiation time with light at 365 nm (Momiji). Measurement was carried out on a 6 µg/ml protein solution. In order to clearly differentiate the situation from that of a mutant, light exchange was carried out with extremely weak light at 365 nm, and the fluorescence spectrum from 470 nm to 650 nm was measured.
Figure 22:
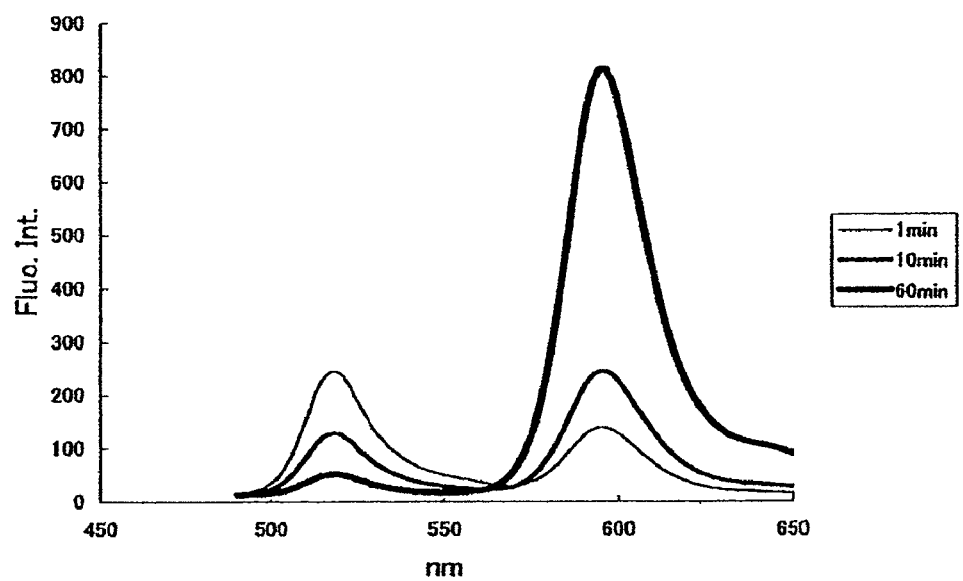
FIG. 22 shows a transition in a change in fluorescence properties depending on irradiation time with light at 365 nm (Momiji 4). Measurement was carried out on a 6 μg/ml protein solution. In order to clearly differentiate the situation from that of a mutant, light exchange was carried out with extremely weak light at 365 nm, and the fluorescence spectrum from 470 nm to 650 nm was measured.
Figure 23:
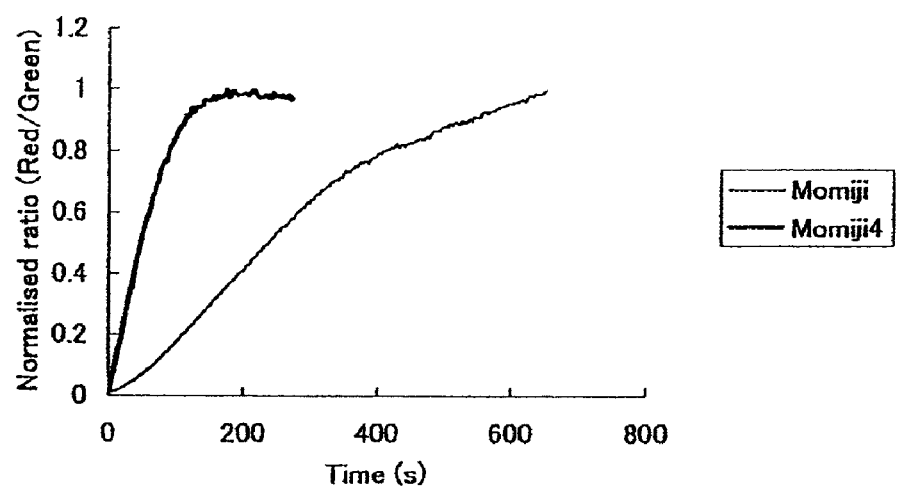
FIG. 23 shows a transition in fluorescence properties in HeLa cells.
Exposure time: 410 nm 100 ms
Green: 400 ms, Red: 50 ms
DM 420DCLP
Green Ex 475AF20, Em 530DF35
Red Ex 550DF35, Em 575ALP
Object lens: X40 Uapo/340

In Momiji, isoleucine (I) at position 197 was substituted with methionine (M). This mutant was named as Momiji 4. The amino acid sequence and nucleotide sequence of Momiji 4 are shown in SEQ ID NOS: 13 and 14, respectively. An ultraviolet ray-irradiation-dependent change in the fluorescence from green to red was observed in Momiji 4 from 1 minute after the irradiation with light at 365 nm. In the wild type (Momiji), however, 10 minutes after the irradiation with light at 365 nm corresponded to 1 minute after the irradiation therewith in Momiji 4. Thus, it was found that Momiji 4 had a light-irradiation-dependent fluorescence properties conversion efficiency that was clearly higher than that of the wild type (Momiji) (FIGS. 16, 20, and 22). Momiji and Momiji 4 were allowed to express in HeLa cells, and a change in fluorescence properties from green to red (red/green) by irradiation with light at 410 nm was measured in the cells. As a result, it was also found that Momiji 4 had higher light-irradiation-dependent fluorescence property conversion efficiency than the wild type. The molecules emitting red fluorescence, whose fluorescence properties ultraviolet ray-irradiation-dependently changed, had pH resistivity lower than that of the wild type (Momiji). The molecules emitting green fluorescence before irradiation with light for conversion of the properties had low pH sensitivity (FIGS. 17 and 19).

Example D-6

Production of Momiji Dimer

By performing electrophoresis (Pseudonative SDS/PAGE) using a 12.5% acrylamide gel without boiling Momiji, it was found that Momiji forms a tetramer. In Momiji, asparagine (N) at position 11 was substituted with arginine (R), leucine (L) at position 29 was substituted with threonine (T), tyrosine (Y) at position 122 was substituted with glutamic acid (E), lysine (K) at position 136 was substituted with asparagine (N), glutamine (Q) at position 138 was substituted with leucine (L), glutamine (Q) at position 142 was substituted with proline (P), asparagine (N) at position 159 was substituted with aspartic acid (D), alanine (A) at position 161 was substituted with serine (S), tyrosine (Y) at position 190 was substituted with threonine (T), phenylalanine (F) at position 192 was substituted with tyrosine (Y), cysteine (C) at position 196 was substituted with serine (S), and 6 amino acids from position 224 to position 229 were deleted. By such operations, the above Momiji became a dimer (FIG. 24). This dimer had fluorescence properties that ultraviolet ray-irradiation-dependently change from green to red, which were equivalent

TABLE 5

| | Fluorescence property mutants | | | | | |
|---|---|---|---|---|---|---|
| Mutant | Excitation maximum before UV irradiation | Fluorescence maximum before UV irradiation | Excitation maximum after UV irradiation | Fluorescence maximum after UV irradiation | Molar absorption coefficient (green) | Molar absorption coefficient (red) |
| Momiji | 508 nm | 518 nm | 578 nm | 588 nm | 102250 (508 nm) | 76950 (578 nm) |
| Momiji 2 | 505 nm | 518 nm | 576 nm | 587 nm | 127200 (505 nm) | 51450 (576 nm) |
| Momiji 4 | 507 nm | 518 nm | 583 nm | 596 nm | 27200 (507 nm) | 32050 (583 nm) | to those of Momiji (FIG. 25). This mutant was named as d16. The amino acid sequence and nucleotide sequence of d16 are shown in SEQ ID NOS: 15 and 16, respectively.

Example D-7

Production of Momiji Monomer

In Momiji, asparagine (N) at position 11 was substituted with arginine (R), leucine (L) at position 29 was substituted with threonine (T), isoleucine (I) at position 95 was substituted with threonine (T), isoleucine (I) at position 101 was substituted with valine (V), isoleucine (I) at position 103 was substituted with threonine (T), tyrosine (Y) at position 122 was substituted with glutamic acid (E), valine (V) at position 124 was substituted with threonine (T), glutamine (Q) at position 138 was substituted with leucine (L), glutamine (Q) at position 142 was substituted with proline (P), asparagine (N) at position 159 was substituted with aspartic acid (D), alanine (A) at position 161 was substituted with serine (S), phenylalanine (F) at position 174 was substituted with methionine (M), tyrosine (Y) at position 190 was substituted with threonine (T), phenylalanine (F) at position 192 was substituted with tyrosine (Y), cysteine (C) at position 196 was substituted with serine (S), phenylalanine (F) at position 212 was substituted with tyrosine (Y), and 6 amino acids from position 224 to position 229 were deleted. By such operations, the above Momiji became a monomer (FIG. 24). This monomer had fluorescence properties that ultraviolet ray-irradiation-dependently change from green to red, which were equivalent to those of Momiji (FIG. 26). This mutant was named as m16. The amino acid sequence and nucleotide sequence of m16 are shown in SEQ ID NOS: 17 and 18, respectively.

INDUSTRIAL APPLICABILITY

The present invention provides novel chromoproteins derived from *Anthopleura inornata*. The chromoprotein of the present invention has certain absorption properties and has low pH sensitivity. Thus, it is useful for molecular biology analysis. In addition, since the absorbance (molecular absorption coefficient) of the chromoprotein of the present invention is significantly high, it enables highly efficient light energy conversion. Moreover, it is also possible to reduce the quantum yield of the chromoprotein of the present invention to close to 1 by genetic engineering techniques. In such a case, a novel fluorescent protein can be produced.

Furthermore, the present invention provides a fluorescent protein having a novel primary structure derived from *Trachyphyllia geoffroyi*. The fluorescent protein of the present invention is characterized in that its color changes from green to red by ultraviolet rays. It is possible to carry out optical marking on specific cells or organs by light. Still further, the present invention provides a fluorescent protein having a novel primary structure derived from *Scolymia vitiensis*. The fluorescent protein of the present invention is characterized in that its color changes from green to red by ultraviolet rays. Thus, it is possible to carry out optical marking on specific cells, organs, or proteins by lights. Still further, the fluorescent protein of the present invention is capable of changing its color from green to red by ultraviolet rays, extremely simply, efficiently, and specifically. This protein is practical because it is extremely stable and bright in both the green and red states before and after the conversion of the color.

What is claimed is:

1. An isolated DNA of either one of following:
   (a) DNA encoding the amino acid sequence shown in SEQ ID NO: 1; and
   (b) DNA encoding a protein which has an amino acid sequence comprising a deletion, substitution and/or addition of one to twenty amino acids with respect to the amino acid sequence shown in SEQ ID NO: 1, and has light-absorbing properties.

2. An isolated DNA having the nucleotide sequence shown in SEQ ID NO: 2.

3. A recombinant vector having the DNA of claim 1.

4. A recombinant vector having the DNA of claim 2.

5. A transformant having the DNA of claim 1.

6. A transformant having the DNA of claim 2.

7. A fusion protein comprising a protein encoded by the DNA of claim 1 and another protein.

8. A fusion protein comprising of a protein encoded by the DNA of claim 2 and another protein.

9. A light-absorbing reagent kit comprising:
   (1) an isolated DNA comprising one of the following:
       (a) DNA encoding the amino acid sequence shown in SEQ ID NO: 1;

(b) DNA encoding a protein which has an amino acid sequence comprising a deletion, substitution and/or addition of one to twenty amino acids with respect to the amino acid sequence shown in SEQ ID NO: 1, and has light-absorbing properties;

(2) a recombinant vector having any of the DNA of 1(a) and 1(b) or
(3) a transformant having any of the DNA of 1(a) and 1(b).

* * * * *

```
                        SEQUENCE LISTING

<160> NUMBER OF SEQ ID NOS: 34

<210> SEQ ID NO 1
<211> LENGTH: 229
<212> TYPE: PRT
<213> ORGANISM: Anthopleura inornata

<400> SEQUENCE: 1

Met Ala Thr Leu Val Lys Glu Thr Met Arg Ile Lys Met Ser Met Glu
1               5                   10                  15

Gly Thr Val Asn Gly His His Phe Lys Cys Glu Gly Gln Gly Glu Gly
                20                  25                  30

Lys Pro Phe Glu Gly Tyr Gln Val Glu Lys Ile Arg Val Thr Glu Gly
            35                  40                  45

Gly Pro Leu Pro Phe Ala Tyr Asp Thr Leu Thr Pro Cys Trp Met Tyr
        50                  55                  60

Gly Ser Lys Thr Phe Ile Lys His Thr Ser Gly Ile Pro Asp Tyr Phe
65                  70                  75                  80

Lys Glu Ser Leu Pro Glu Gly Phe Thr Trp Glu Arg Thr Gln Ile Tyr
                85                  90                  95

Glu Asp Gly Gly Cys Leu Thr Ile His Gln Asp Thr Ser Met Gln Gly
                100                 105                 110

Asp Cys Phe Ile Phe Lys Ile Lys Val Ile Gly Thr Asn Phe Pro Ala
            115                 120                 125
```

Asn Gly Pro Val Met Gln Lys Lys Thr Ala Gly Trp Glu Pro Cys Val
    130                 135                 140

Glu Met Leu Tyr Pro Arg Ala Gly Val Leu Cys Gly Gln Ser Leu Met
145                 150                 155                 160

Ala Leu Lys Cys Lys Asp Gly Asn His Leu Thr Cys His Leu Arg Thr
                165                 170                 175

Thr Tyr Arg Ser Arg Lys Ala Gly Gln Lys Met Pro Glu Phe His Phe
            180                 185                 190

Gly Asp His Arg Ile Glu Ile Leu Lys Glu Glu Gln Gly Met Arg
        195                 200                 205

Ile Glu Gln Tyr Glu Ala Ala Val Ala Arg Tyr Cys Glu Ala Pro Ser
    210                 215                 220

Arg Leu Gly His His
225

<210> SEQ ID NO 2
<211> LENGTH: 690
<212> TYPE: DNA
<213> ORGANISM: Anthopleura inornata

<400> SEQUENCE: 2
atggctacct tggttaaaga aactatgcgc atcaagatga gtatggaagg gacggttaat     60
ggacaccact tcaagtgtga aggacaagga gagggcaagc cttttgaagg ttaccaggtc    120
gaaaagatta gagttactga aggaggtccg ctacccttg cgtacgatac tttgacacct    180
tgctggatgt atggaagtaa aaccttcatc aagcatacat caggaattcc cgattacttc    240
aaggagtctc ttcctgaagg ctttacttgg gaaagaacgc aaatctacga ggatggaggc    300
tgtcttacta ttcaccagga cacaagcatg cagggagatt gttttatttt caagataaaa    360
gtcattggta ccaactttcc tgccaatggt cccgtgatgc agaagaaaac agcaggatgg    420
gagccatgcg ttgagatgct ttatcctcgt gccggtgtct tgtgtggaca gtcgttgatg    480
gccctgaaat gcaaggatgg caaccacctg acgtgccatc tgcgaactac ctacaggtcc    540
agaaaggcag gacaaaaaat gccagagttc catttcgggg atcatcgtat tgagatcctg    600
aaggaagaag aacaaggcat gcgtattgaa caatacgagg cagcggtggc gaggtactgc    660
gaagctccat ccaggcttgg acatcactaa                                    690

<210> SEQ ID NO 3
<211> LENGTH: 229
<212> TYPE: PRT
<213> ORGANISM: Anthopleura inornata

<400> SEQUENCE: 3

Met Ala Thr Leu Val Lys Glu Thr Met Arg Ile Lys Met Ser Met Glu
1               5                   10                  15

Gly Thr Val Asn Gly His His Phe Lys Cys Glu Gly Gln Gly Glu Gly
            20                  25                  30

Lys Pro Phe Glu Gly Tyr Gln Val Glu Lys Ile Arg Val Thr Glu Gly
        35                  40                  45

Gly Pro Leu Pro Phe Ala Tyr Asp Ile Leu Ala Pro Cys Cys Ser Tyr
    50                  55                  60

Gly Ser Lys Thr Phe Ile Lys His Val Ser Gly Ile Pro Asp Tyr Phe
65                  70                  75                  80

Lys Glu Ser Phe Pro Glu Gly Phe Thr Trp Glu Arg Thr Gln Ile Tyr
                85                  90                  95

```
Glu Asp Gly Gly Ser Leu Ser Ile His Gln Asp Thr Ser Leu Gln Gly
            100                 105                 110

Asp Cys Phe Ile Tyr Lys Ile Lys Val Ile Gly Thr Asn Phe Pro Ala
            115                 120                 125

Asn Gly Pro Val Met Gln Lys Lys Thr Ala Gly Trp Glu Pro Cys Val
        130                 135                 140

Glu Met Leu Tyr Pro Arg Ala Gly Val Leu Cys Gly Gln Ser Leu Met
145                 150                 155                 160

Ala Leu Lys Cys Lys Asp Gly Asn His Leu Thr Cys His Leu Arg Thr
                165                 170                 175

Thr Tyr Arg Ser Arg Lys Ala Gly Gln Lys Met Pro Glu Phe His Phe
            180                 185                 190

Gly Asp His Arg Ile Glu Ile Leu Lys Glu Glu Glu Gln Gly Met Arg
            195                 200                 205

Ile Glu Gln Tyr Glu Ala Ala Val Ala Arg Tyr Cys Glu Ala Pro Ser
        210                 215                 220

Arg Leu Gly His His
225
```

<210> SEQ ID NO 4
<211> LENGTH: 690
<212> TYPE: DNA
<213> ORGANISM: Anthopleura inornata

<400> SEQUENCE: 4

```
atggctacct tggttaaaga aactatgcgc atcaagatga gtatggaagg gacggttaat      60
ggacaccact tcaagtgtga aggacaagga gagggcaagc cttttgaagg ttaccaggtc     120
gaaaagatta gagttactga aggaggtccg ctacccttttg cgtacgatat tttggcacct    180
tgctgctcgt atggaagtaa aaccttcatc aagcatgtct cgggaatccc cgattacttc     240
aaggagtcct ccctgaaggc tttacttgg gaaagaacgc aaatctacga ggatggaggc      300
tctctttcta ttcaccagga cacaagcctg cagggagatt gttttattta caagatcaaa    360
gtcattggca ccaactttcc tgccaatggt cccgtgatgc agaagaaaac agcaggatgg    420
gagccatgcg ttgagatgct ttatcctcgt gccggtgtct tgtgtggaca gtcgttgatg    480
gccctgaaat gcaaggatgg caaccacctg acgtgccatc tgcgaactac ctacaggtcc    540
agaaaggcag acaaaaaat gccagagttc catttcgggg atcatcgtat tgagatcctg     600
aaggaagaag aacaaggcat gcgtattgaa caatacgagg cagcggtggc gaggtactgc    660
gaagctccat ccaggcttgg acatcactaa                                       690
```

<210> SEQ ID NO 5
<211> LENGTH: 225
<212> TYPE: PRT
<213> ORGANISM: Trachyphyllia geoffroyi

<400> SEQUENCE: 5

```
Met Ser Leu Ile Lys Pro Glu Met Lys Ile Lys Leu Leu Met Glu Gly
1               5                   10                  15

Asn Val Asn Gly His Gln Phe Val Ile Glu Gly Asp Gly Lys Gly His
            20                  25                  30

Pro Phe Glu Gly Lys Gln Ser Met Asp Leu Val Val Lys Glu Gly Ala
        35                  40                  45

Pro Leu Pro Phe Ala Tyr Asp Ile Leu Thr Thr Ala Phe His Tyr Gly
    50                  55                  60
```

```
Asn Arg Val Phe Ala Lys Tyr Pro Asp His Ile Pro Asp Tyr Phe Lys
 65                  70                  75                  80

Gln Ser Phe Pro Lys Gly Phe Ser Trp Glu Arg Ser Leu Met Phe Glu
                 85                  90                  95

Asp Gly Gly Val Cys Ile Ala Thr Asn Asp Ile Thr Leu Lys Gly Asp
            100                 105                 110

Thr Phe Phe Asn Lys Val Arg Phe Asp Gly Val Asn Phe Pro Pro Asn
        115                 120                 125

Gly Pro Val Met Gln Lys Lys Thr Leu Lys Trp Glu Ala Ser Thr Glu
    130                 135                 140

Lys Met Tyr Leu Arg Asp Gly Val Leu Thr Gly Asp Ile Thr Met Ala
145                 150                 155                 160

Leu Leu Leu Lys Gly Asp Val His Tyr Arg Cys Asp Phe Arg Thr Thr
                165                 170                 175

Tyr Lys Ser Arg Gln Glu Gly Val Lys Leu Pro Gly Tyr His Phe Val
            180                 185                 190

Asp His Cys Ile Ser Ile Leu Arg His Asp Lys Asp Tyr Asn Glu Val
        195                 200                 205

Lys Leu Tyr Glu His Ala Val Ala His Ser Gly Leu Pro Asp Asn Val
    210                 215                 220

Lys
225

<210> SEQ ID NO 6
<211> LENGTH: 678
<212> TYPE: DNA
<213> ORGANISM: Trachyphyllia geoffroyi

<400> SEQUENCE: 6
atgagtctga ttaaaccaga aatgaagatc aagctgctta tggaaggcaa tgtaaacggg     60
caccagtttg ttattgaggg agatggaaaa ggccatcctt ttgagggaaa acagagtatg    120
gaccttgtag tcaaagaagg cgcacctctc ccttttgcct acgatatctt gacaacagca    180
ttccattatg gtaacagggt ttttgctaaa tacccagacc atataccaga ctacttcaag    240
cagtcgtttc ccaaagggtt ttcttgggag cgaagcctga tgttcgagga cgggggcgtt    300
tgcatcgcta caaatgacat aacactgaaa ggagacactt ttttaacaa agttcgattt     360 gatggcgtaa actttccccc aaatggtcct gttatgcaga agaagactct gaaatgggag    420
gcatccactg agaaaatgta tttgcgtgat ggagtgttga cgggcgatat taccatggct    480
ctgctgctta aaggagatgt ccattaccga tgtgacttca gaactactta caaatctagg    540
caggagggtg tcaagttgcc aggatatcac tttgtcgatc actgcatcag catattgagg    600
catgacaaag actacaacga ggttaagctg tatgagcatg ctgttgccca ttctggattg    660
ccggacaacg tcaagtaa                                                  678

<210> SEQ ID NO 7
<211> LENGTH: 225
<212> TYPE: PRT
<213> ORGANISM: Trachyphyllia geoffroyi

<400> SEQUENCE: 7

Met Ser Leu Ile Lys Pro Glu Met Lys Ile Lys Leu Leu Met Glu Gly
 1                5                  10                  15

Asn Val Asn Gly His Gln Phe Val Ile Glu Gly Asp Gly Lys Gly His
                 20                  25                  30
```

Pro Phe Glu Gly Lys Gln Ser Met Asp Leu Val Val Lys Glu Gly Ala
            35                  40                  45

Pro Leu Pro Phe Ala Tyr Asp Ile Leu Thr Thr Ala Phe His Tyr Gly
        50                  55                  60

Asn Arg Val Phe Ala Lys Tyr Pro Asp His Ile Pro Asp Tyr Phe Lys
65                  70                  75                  80

Gln Ser Phe Pro Lys Gly Phe Ser Trp Glu Arg Ser Leu Met Phe Glu
                85                  90                  95

Asp Gly Gly Val Cys Ile Ala Thr Asn Asp Ile Thr Leu Lys Gly Asp
            100                 105                 110

Thr Phe Phe Asn Lys Val Arg Phe Asp Gly Val Asn Phe Pro Pro Asn
        115                 120                 125

Gly Pro Val Met Gln Lys Lys Thr Leu Lys Trp Glu Ala Ser Thr Glu
    130                 135                 140

Lys Met Tyr Leu Arg Asp Gly Val Leu Thr Gly Asp Ile Arg Met Glu
145                 150                 155                 160

Leu Leu Leu Lys Gly Asp Val His Tyr Arg Cys Asp Phe Arg Thr Thr
                165                 170                 175

Tyr Lys Ser Arg Gln Glu Gly Val Lys Leu Pro Gly Tyr His Phe Val
            180                 185                 190

Asp His Cys Ile Ser Ile Leu Arg His Asp Lys Asp Tyr Asn Glu Val
        195                 200                 205

Lys Leu Tyr Glu His Ala Val Ala His Ser Gly Leu Pro Asp Asn Val
    210                 215                 220

Lys
225

<210> SEQ ID NO 8
<211> LENGTH: 678
<212> TYPE: DNA
<213> ORGANISM: Trachyphyllia geoffroyi

<400> SEQUENCE: 8
atgagtctga ttaaaccaga aatgaagatc aagctgctta tggaaggcaa tgtaaacggg    60
caccagtttg ttattgaggg agatggaaaa ggccatcctt ttgagggaaa acagagtatg   120
gaccttgtag tcaagaagg cgcacctctc cctttgcct acgatatctt gacaacagca   180
ttccattatg gtaacagggt ttttgctaaa tacccagacc atataccaga ctacttcaag   240
cagtcgtttc ccaagggtt ttcttgggag cgaagcctga tgttcgagga cgggggcgtt   300
tgcatcgcta caaatgacat aacactgaaa ggagacactt ttttaacaa agttcgattt   360 gatggcgtaa actttccccc aaatggtcct gttatgcaga agaagactct gaaatgggag   420
gcatccactg agaaaatgta tttgcgtgat ggagtgttga cgggcgatat taggatggag   480
ctgctgctta aggagatgt ccattaccga tgtgacttca gaactactta caaatctagg   540
caggagggtg tcaagttgcc aggatatcac tttgtcgatc actgcatcag catattgagg   600
catgacaaag actacaacga ggttaagctg tatgagcatg ctgttgccca ttctggattg   660
ccggacaacg tcaagtaa                                                 678

<210> SEQ ID NO 9
<211> LENGTH: 229
<212> TYPE: PRT
<213> ORGANISM: Scolymia vitiensis

<400> SEQUENCE: 9

```
Met Val Ser Val Ile Lys Asp Glu Met Lys Val Asn Leu Arg Met Glu
1               5                   10                  15

Gly Ser Val Asn Gly His Asp Phe Val Ile Asp Gly Leu Gly Ser Gly
            20                  25                  30

Lys Pro Lys Glu Gly Thr Gln Thr Ile Glu Leu Lys Val Val Lys Gly
        35                  40                  45

Gly Pro Leu Pro Phe Ala Tyr Asp Ile Leu Thr Thr Ala Phe His Tyr
    50                  55                  60

Gly Asn Arg Val Phe Ala Lys Tyr Pro Lys Asp Ile Pro Asn Tyr Phe
65                  70                  75                  80

Glu Gln Ser Phe Pro Glu Gly Tyr Ser Trp Glu Arg Ser Met Ile Phe
                85                  90                  95

Glu Asp Gly Gly Ile Cys Ile Ala Arg Asn Asp Ile Thr Met Asp Gly
            100                 105                 110

Gly Thr Phe Tyr Asn Lys Val Arg Phe Tyr Gly Val Asn Phe Pro Pro
        115                 120                 125

Asn Gly Pro Val Met Gln Lys Lys Thr Gln Lys Trp Glu Gln Ser Thr
    130                 135                 140

Glu Lys Met Tyr Ala Arg Asp Gly Val Leu Thr Gly Asp Ile Asn Met
145                 150                 155                 160

Ala Leu Leu Leu Lys Gly Gly His Tyr Arg Cys Asp Phe Arg Thr
                165                 170                 175

Thr Phe Lys Ala Lys Glu Lys Gly Val Lys Leu Pro Gly Tyr His Phe
            180                 185                 190

Ile Asp His Cys Ile Glu Ile Leu Ser His Arg Asn Asp Tyr Asn Asn
            195                 200                 205

Val Thr Leu Phe Glu His Ala Val Ala Arg Ser Gly Leu Gln Asp Lys
        210                 215                 220

Glu Lys Gln Gln Gln
225

<210> SEQ ID NO 10
<211> LENGTH: 690
<212> TYPE: DNA
<213> ORGANISM: Scolymia vitiensis

<400> SEQUENCE: 10
atggtgagtg tgattaagga cgaaatgaaa gtcaacctgc gtatggaagg cagtgtaaac      60
ggacacgact cgtgattga cggacttggt tcaggcaagc ctaaagaggg aacacagact     120
attgagctta agtcgtaaa gggtggacct ttaccttcg cctacgatat cctgacaaca      180
gcattccatt acggcaaccg ggtattcgcc aaatacccaa aggatatacc aaactatttc     240
gagcagtcgt tcctgaggg gtattcgtgg aacggagca tgattttcga agacggggc       300
atttgcatcg ctagaaacga cataacaatg gatggtggca ctttctataa taagtttcga     360
ttttatggtg taaatttccc ccccaatggt ccagttatgc agaagaagac gcagaaatgg     420
gagcaatcca ctgagaaaat gtatgcgcgt gatggagtgt tgacgggtga tattaacatg     480
gctctgttgc ttaaaggggg tggccattac cgatgtgact tcagaactac tttcaaagct     540
aaggagaagg gtgtcaagtt gccaggctac cactttatag atcactgcat agagatttta     600
agccatcgca acgattacaa caacgttacg ctttttgagc atgctgttgc tcgttctgga     660
ttgcaggaca aagagaaaca acaacaatga                                      690

<210> SEQ ID NO 11
```

<211> LENGTH: 229
<212> TYPE: PRT
<213> ORGANISM: Scolymia vitiensis

<400> SEQUENCE: 11

```
Met Val Ser Val Ile Lys Asp Glu Met Lys Val Asn Leu Arg Met Glu
1               5                   10                  15
Gly Ser Val Asn Gly His Asp Phe Val Ile Asp Gly Leu Gly Ser Gly
            20                  25                  30
Lys Pro Lys Glu Gly Thr Gln Thr Ile Glu Leu Lys Val Val Lys Gly
        35                  40                  45
Gly Pro Leu Pro Phe Ala Tyr Asp Ile Leu Thr Thr Ala Phe His Tyr
    50                  55                  60
Gly Asn Arg Val Phe Ala Lys Tyr Pro Lys Asp Ile Pro Asn Tyr Phe
65                  70                  75                  80
Glu Gln Ser Phe Pro Lys Gly Tyr Ser Trp Glu Arg Ser Met Ile Phe
                85                  90                  95
Glu Asp Gly Gly Ile Cys Ile Ala Arg Asn Asp Ile Thr Met Glu Gly
            100                 105                 110
Gly Thr Phe Tyr Asn Lys Val Arg Phe Tyr Gly Val Asn Phe Pro Pro
        115                 120                 125
Asn Gly Pro Val Met Gln Lys Lys Thr Gln Lys Trp Glu Pro Ser Thr
    130                 135                 140
Glu Lys Met Tyr Ala Arg Asp Gly Val Leu Thr Gly Asp Ile Asn Met
145                 150                 155                 160
Ala Leu Leu Leu Lys Gly Gly His Tyr Arg Cys Asp Phe Arg Thr
                165                 170                 175
Thr Phe Lys Ala Lys Glu Lys Gly Val Lys Leu Pro Gly Tyr His Phe
            180                 185                 190
Ile Asp His Cys Ile Glu Ile Leu Ser His His Asn Asp Tyr Asn Asn
        195                 200                 205
Val Thr Leu Phe Glu His Ala Val Ala Arg Ser Gly Leu Gln Asp Lys
    210                 215                 220
Glu Lys Gln Gln Gln
225
```

<210> SEQ ID NO 12
<211> LENGTH: 690
<212> TYPE: DNA
<213> ORGANISM: Scolymia vitiensis

<400> SEQUENCE: 12

```
atggtgagtg tgattaagga cgaaatgaaa gtcaacctgc gtatggaagg cagtgtaaac    60
ggacacgact tcgtgattga cggacttggt tcaggcaagc ctaaagaggg aacacagact   120
attgagctta aagtcgtaaa gggtggacct ttacctttcg cctacgatat cctgacaaca   180
gcattccatt acggcaaccg ggtattcgcc aaatacccaa aggatatacc aaactatttc   240
gagcagtcgt tcctaaaggg gtattcgtgg aacggagca tgattttcga agacgggggc   300
atttgcatcg ccagaaacga cataacaatg gaaggtggca ctttctataa taagttcga   360
ttttatggtg taaacttccc ccccaatggt ccagttatgc agaagaagac gcagaagtgg   420
gagccatcca ctgagaaaat gtatgcgcgt gatggagtgt tgacgggtga tattaacatg   480
gctctgttgc ttaaaggggg tggccattac cgatgtgact tcagaactac tttcaaagct   540
aaggagaagg gtgtcaagtt gccaggctac cactttatag atcactgcat agagatttta   600
```

```
agccatcaca acgattacaa caacgttacg cttttttgagc atgctgttgc tcgttctgga    660
ttgcaggaca aagagaaaca acaacaatga                                     690
```

<210> SEQ ID NO 13
<211> LENGTH: 229
<212> TYPE: PRT
<213> ORGANISM: Scolymia vitiensis

<400> SEQUENCE: 13

```
Met Val Ser Val Ile Lys Asp Glu Met Lys Val Asn Leu Arg Met Glu
1               5                   10                  15

Gly Ser Val Asn Gly His Asp Phe Val Ile Asp Gly Leu Gly Ser Gly
            20                  25                  30

Lys Pro Lys Glu Gly Thr Gln Thr Ile Glu Leu Lys Val Val Lys Gly
        35                  40                  45

Gly Pro Leu Pro Phe Ala Tyr Asp Ile Leu Thr Thr Ala Phe His Tyr
    50                  55                  60

Gly Asn Arg Val Phe Ala Lys Tyr Pro Lys Asp Ile Pro Asn Tyr Phe
65                  70                  75                  80

Glu Gln Ser Phe Pro Glu Gly Tyr Ser Trp Glu Arg Ser Met Ile Phe
                85                  90                  95

Glu Asp Gly Gly Ile Cys Ile Ala Arg Asn Asp Ile Thr Met Asp Gly
            100                 105                 110

Gly Thr Phe Tyr Asn Lys Val Arg Phe Tyr Gly Val Asn Phe Pro Pro
        115                 120                 125

Asn Gly Pro Val Met Gln Lys Thr Gln Lys Trp Glu Gln Ser Thr
    130                 135                 140

Glu Lys Met Tyr Ala Arg Asp Gly Val Leu Thr Gly Asp Ile Asn Met
145                 150                 155                 160

Ala Leu Leu Leu Lys Gly Gly His Tyr Arg Cys Asp Phe Arg Thr
                165                 170                 175

Thr Phe Lys Ala Lys Glu Lys Gly Val Lys Leu Pro Gly Tyr His Phe
            180                 185                 190

Ile Asp His Cys Met Glu Ile Leu Ser His Arg Asn Asp Tyr Asn Asn
        195                 200                 205

Val Thr Leu Phe Glu His Ala Val Ala Arg Ser Gly Leu Gln Asp Lys
    210                 215                 220

Glu Lys Gln Gln Gln
225
```

<210> SEQ ID NO 14
<211> LENGTH: 690
<212> TYPE: DNA
<213> ORGANISM: Scolymia vitiensis

<400> SEQUENCE: 14

```
atggtgagtg tgattaagga cgaaatgaaa gtcaacctgc gtatggaagg cagtgtaaac    60
ggacacgact tcgtgattga cggacttggt tcaggcaagc ctaaagaggg aacacagact   120
attgagctta aagtcgtaaa gggtggacct ttacctttcg cctacgatat cctgacaaca   180
gcattccatt acggcaaccg ggtattcgcc aaatacccaa aggatatacc aaactatttc   240
gagcagtcgt ttcctgaggg gtattcgtgg gaacggagca tgattttcga agacgggggc   300
atttgcatcg ctagaaacga cataacaatg gatggtggca cttttctataa taaagttcga   360 ttttatggtg taaatttccc ccccaatggt ccagttatgc agaagaagac gcagaaatgg   420
```

-continued

```
gagcaatcca ctgagaaaat gtatgcgcgt gatggagtgt tgacgggtga tattaacatg    480
gctctgttgc ttaaagggg tggccattac cgatgtgact tcagaactac tttcaaagct    540
aaggagaagg gtgtcaagtt gccaggctac cactttatag atcactgcat ggagatttta    600
agccatcgca acgattacaa caacgttacg cttttttgagc atgctgttgc tcgttctgga    660
ttgcaggaca agagaaaca acaacaatga                                      690
```

<210> SEQ ID NO 15
<211> LENGTH: 223
<212> TYPE: PRT
<213> ORGANISM: Scolymia vitiensis

<400> SEQUENCE: 15

```
Met Val Ser Val Ile Lys Asp Glu Met Lys Val Arg Leu Arg Met Glu
1               5                   10                  15

Gly Ser Val Asn Gly His Asp Phe Val Ile Asp Gly Thr Gly Ser Gly
                20                  25                  30

Lys Pro Lys Glu Gly Thr Gln Thr Ile Glu Leu Lys Val Val Lys Gly
            35                  40                  45

Gly Pro Leu Pro Phe Ala Tyr Asp Ile Leu Thr Thr Ala Phe His Tyr
        50                  55                  60

Gly Asn Arg Val Phe Ala Lys Tyr Pro Lys Asp Ile Pro Asn Tyr Phe
65                  70                  75                  80

Glu Gln Ser Phe Pro Glu Gly Tyr Ser Trp Glu Arg Ser Met Ile Phe
                85                  90                  95

Glu Asp Gly Gly Ile Cys Ile Ala Arg Asn Asp Ile Thr Met Asp Gly
            100                 105                 110

Gly Thr Phe Tyr Asn Lys Val Arg Phe Glu Gly Val Asn Phe Pro Pro
        115                 120                 125

Asn Gly Pro Val Met Gln Lys Asn Thr Leu Lys Trp Glu Pro Ser Thr
130                 135                 140

Glu Lys Met Tyr Ala Arg Asp Gly Val Leu Thr Gly Asp Ile Asp Met
145                 150                 155                 160

Ser Leu Leu Leu Lys Gly Gly His Tyr Arg Cys Asp Phe Arg Thr
                165                 170                 175

Thr Phe Lys Ala Lys Glu Lys Gly Val Lys Leu Pro Gly Thr His Tyr
            180                 185                 190

Ile Asp His Ser Ile Glu Ile Leu Ser His Arg Asn Asp Tyr Asn Asn
        195                 200                 205

Val Thr Leu Phe Glu His Ala Val Ala Arg Ser Gly Leu Gln Asp
    210                 215                 220
```

<210> SEQ ID NO 16
<211> LENGTH: 672
<212> TYPE: DNA
<213> ORGANISM: Scolymia vitiensis

<400> SEQUENCE: 16

```
atggtgagtg tgattaagga cgaaatgaaa gtccgcctgc gtatggaagg cagtgtaaac    60
ggacacgact tcgtgattga cggaactggt tcaggcaagc ctaaagaggg aacacagact   120
attgagctta agtcgtaaa gggtggacct ttacctttcg cctacgatat cctgacaaca   180
gcattccatt acggcaaccg ggtattcgcc aaatacccaa aggatatacc aaactatttc   240
gagcagtcgt ttcctgaggg gtattcgtgg gaacggagct gattttcga agacgggggc   300 atttgcatcg ctagaaacga cataacaatg gatggtggca ctttctataa taaagttcga   360
```

-continued

```
tttgaaggtg taaatttccc ccccaatggt ccagttatgc agaagaatac gctgaaatgg    420
gagccatcca ctgagaaaat gtatgcgcgt gatggagtgt tgacgggtga tattgacatg    480
tccctgttgc ttaaggggg tggccattac cgatgtgact tcagaactac tttcaaagct    540
aaggagaagg gtgtcaagtt gccaggcacc cactacatag atcacagcat agagatttta    600
agccatcgca acgattacaa caacgttacg cttttgagc atgctgttgc tcgttctgga     660
ttgcaggact aa                                                         672
```

<210> SEQ ID NO 17
<211> LENGTH: 223
<212> TYPE: PRT
<213> ORGANISM: Scolymia vitiensis

<400> SEQUENCE: 17

```
Met Val Ser Val Ile Lys Asp Glu Met Lys Val Arg Leu Arg Met Glu
1               5                   10                  15

Gly Ser Val Asn Gly His Asp Phe Val Ile Asp Gly Thr Gly Ser Gly
            20                  25                  30

Lys Pro Lys Glu Gly Thr Gln Thr Ile Glu Leu Lys Val Val Lys Gly
        35                  40                  45

Gly Pro Leu Pro Phe Ala Tyr Asp Ile Leu Thr Thr Ala Phe His Tyr
    50                  55                  60

Gly Asn Arg Val Phe Ala Lys Tyr Pro Lys Asp Ile Pro Asn Tyr Phe
65                  70                  75                  80

Glu Gln Ser Phe Pro Glu Gly Tyr Ser Trp Glu Arg Ser Met Thr Phe
                85                  90                  95

Glu Asp Gly Gly Val Cys Thr Ala Arg Asn Asp Ile Thr Met Asp Gly
            100                 105                 110

Gly Thr Phe Tyr Asn Lys Val Arg Phe Glu Gly Thr Asn Phe Pro Pro
        115                 120                 125

Asn Gly Pro Val Met Gln Lys Lys Thr Leu Lys Trp Glu Pro Ser Thr
    130                 135                 140

Glu Lys Met Tyr Ala Arg Asp Gly Val Leu Thr Gly Asp Ile Asp Met
145                 150                 155                 160

Ser Leu Leu Leu Lys Gly Gly Gly His Tyr Arg Cys Asp Met Arg Thr
                165                 170                 175

Thr Phe Lys Ala Lys Glu Lys Gly Val Lys Leu Pro Gly Thr His Tyr
            180                 185                 190

Ile Asp His Ser Ile Glu Ile Leu Ser His Arg Asn Asp Tyr Asn Asn
        195                 200                 205

Val Thr Leu Tyr Glu His Ala Val Ala Arg Ser Gly Leu Gln Asp
    210                 215                 220
```

<210> SEQ ID NO 18
<211> LENGTH: 672
<212> TYPE: DNA
<213> ORGANISM: Scolymia vitiensis

<400> SEQUENCE: 18

```
atggtgagtg tgattaagga cgaaatgaaa gtccgcctgc gtatggaagg cagtgtaaac    60
ggacacgact tcgtgattga cggaactggt tcaggcaagc ctaaagaggg aacacagact    120
attgagctta agtcgtaaa gggtggacct tacctttcg cctacgatat cctgacaaca     180
gcattccatt acggcaaccg ggtattcgcc aaatacccaa aggatatacc aaactatttc    240
```

```
gagcagtcgt tccctgaggg gtattcgtgg gaacggagca tgactttcga agacgggggc    300
gtttgcaccg ctagaaacga cataacaatg gatggtggca ctttctataa taaagttcga    360
tttgaaggta caaatttccc ccccaatggt ccagttatgc agaagaagac gctgaaatgg    420
gagccatcca ctgagaaaat gtatgcgcgt gatgagtgt tgacgggtga tattgacatg     480
tccctgttgc ttaaaggggg tggccattac cgatgtgaca tgagaactac tttcaaagct    540
aaggagaagg gtgtcaagtt gccaggcacc cactacatag atcacagcat agagattta    600 agccatcgca acgattacaa caacgttacg ctttatgagc atgctgttgc tcgttctgga    660
ttgcaggact aa                                                        672

<210> SEQ ID NO 19
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: r is a or g
<220> FEATURE:
<221> NAME/KEY: misc_feature
<222> LOCATION: (9)..(9)
<223> OTHER INFORMATION: y is c or t
<220> FEATURE:
<221> NAME/KEY: misc_feature
<222> LOCATION: (18)..(18)
<223> OTHER INFORMATION: r is a or g

<400> SEQUENCE: 19
gaaggrtgyg tcaayggrca y                                              21

<210> SEQ ID NO 20
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: v is a, c, or g
<220> FEATURE:
<221> NAME/KEY: misc_feature
<222> LOCATION: (6)..(6)
<223> OTHER INFORMATION: d is a, g, or t
<220> FEATURE:
<221> NAME/KEY: misc_feature
<222> LOCATION: (11)..(11)
<223> OTHER INFORMATION: y is c or t
<220> FEATURE:
<221> NAME/KEY: misc_feature
<222> LOCATION: (12)..(12)
<223> OTHER INFORMATION: d is a, g, or t
<220> FEATURE:
<221> NAME/KEY: misc_feature
<222> LOCATION: (14)..(14)
<223> OTHER INFORMATION: v is a, c, or g
<220> FEATURE:
<221> NAME/KEY: misc_feature
<222> LOCATION: (21)..(21)
<223> OTHER INFORMATION: r is a or g

<400> SEQUENCE: 20
acvggdccat ydgvaagaaa rtt                                            23

<210> SEQ ID NO 21
<211> LENGTH: 36
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is inosine
<220> FEATURE:
<221> NAME/KEY: misc_feature
<222> LOCATION: (29)..(30)
<223> OTHER INFORMATION: n is inosine
<220> FEATURE:
<221> NAME/KEY: misc_feature
<222> LOCATION: (34)..(35)
<223> OTHER INFORMATION: n is inosine

<400> SEQUENCE: 21
ggccacgcgt cgactagtac gggnngggnn gggnng                              36

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
aagagactcc ttgaagtaat cggga                                          25

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ggccacgcgt cgactagtac                                                20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
aaaatatcgt acgcaaaggg                                                20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
aggaggtccg ctacccttttg                                               20

<210> SEQ ID NO 26
<211> LENGTH: 33
<212> TYPE: DNA
<213> ORGANISM: Artificial Sequence
<220> FEATURE:
<223> OTHER INFORMATION: primer

<400> SEQUENCE: 26
```
cccggatccg accatggcta ccttggttaa aga          33

<210> SEQ ID NO 27
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (7)..(7)
<223> OTHER INFORMATION: n is a, g, c, or t
<220> FEATURE:
<221> NAME/KEY: misc_feature
<222> LOCATION: (9)..(9)
<223> OTHER INFORMATION: n is a, g, c, or t
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (11)..(11)
<223> OTHER INFORMATION: r is a or g
<220> FEATURE:
<221> NAME/KEY: misc_feature
<222> LOCATION: (12)..(12)
<223> OTHER INFORMATION: y is c or t

<400> SEQUENCE: 27
atcaagntnw ryatggaagg          20

<210> SEQ ID NO 28
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: v is a, c, or g
<220> FEATURE:
<221> NAME/KEY: misc_feature
<222> LOCATION: (6)..(6)
<223> OTHER INFORMATION: d is a, g, or t
<220> FEATURE:
<221> NAME/KEY: misc_feature
<222> LOCATION: (11)..(11)
<223> OTHER INFORMATION: y is c or t
<220> FEATURE:
<221> NAME/KEY: misc_feature
<222> LOCATION: (12)..(12)
<223> OTHER INFORMATION: d is a, g, or t
<220> FEATURE:
<221> NAME/KEY: misc_feature
<222> LOCATION: (14)..(14)
<223> OTHER INFORMATION: v is a, c, or g
<220> FEATURE:
<221> NAME/KEY: misc_feature
<222> LOCATION: (21)..(21)
<223> OTHER INFORMATION: r is a or g

<400> SEQUENCE: 28
acvggdccat ydgvaagaaa rtt          23

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29

```
agttcacacc atgatattca atatcata                                          28

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ggccacgcgt cgactagtac                                                   20

<210> SEQ ID NO 31
<211> LENGTH: 23
<212> TYPE: DNA
<213> ORGANISM: Artificial Sequence
<220> FEATURE:
<223> OTHER INFORMATION: primer

<400> SEQUENCE: 31
tcttcgtaag tcatgcttcg ttc                                               23

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
ggtattcgcc aaatacccaa a                                                 21

<210> SEQ ID NO 33
<211> LENGTH: 40
<212> TYPE: DNA
<213> ORGANISM: Artificial Sequence
<220> FEATURE:
<223> OTHER INFORMATION: primer

<400> SEQUENCE: 33
cccggatccg accatggtga gtgtgattaa ggacgaaatg                             40

<210> SEQ ID NO 34
<211> LENGTH: 33
<212> TYPE: DNA
<213> ORGANISM: Artificial Sequence
<220> FEATURE:
<223> OTHER INFORMATION: primer

<400> SEQUENCE: 34
ccgctcgagt tgttgttgtt tctctttgtc ctg                                    33
```